United States Patent
Wang et al.

(10) Patent No.: US 11,236,052 B2
(45) Date of Patent: Feb. 1, 2022

(54) AMINOBENZIMIDAZOLE DERIVATIVES, TREATMENTS, AND METHODS OF INHIBITING HISTONE DEACETYLASE

(71) Applicant: TRANSLATIONAL DRUG DEVELOPMENT, LLC, Scottsdale, AZ (US)

(72) Inventors: Tong Wang, Scottsdale, AZ (US); Stephen Gately, Scottsdale, AZ (US)

(73) Assignee: Translational Drug Development, LLC, Scottsdale, AZ (US)

( * ) Notice: Subject to any disclaimer, the term of this patent is extended or adjusted under 35 U.S.C. 154(b) by 0 days.

(21) Appl. No.: 16/644,457

(22) PCT Filed: Sep. 6, 2018

(86) PCT No.: PCT/US2018/049801
§ 371 (c)(1),
(2) Date: Mar. 4, 2020

(87) PCT Pub. No.: WO2019/051125
PCT Pub. Date: Mar. 14, 2019

(65) Prior Publication Data
US 2021/0061770 A1    Mar. 4, 2021

Related U.S. Application Data

(60) Provisional application No. 62/554,728, filed on Sep. 6, 2017.

(51) Int. Cl.
*C07D 235/30* (2006.01)
*C07D 405/06* (2006.01)
*A61P 35/00* (2006.01)

(52) U.S. Cl.
CPC ............ *C07D 235/30* (2013.01); *A61P 35/00* (2018.01); *C07D 405/06* (2013.01)

(58) Field of Classification Search
CPC .......................... C07D 235/30; C07D 405/06
See application file for complete search history.

(56) References Cited

U.S. PATENT DOCUMENTS

| | | |
|---|---|---|
| 9,221,801 B2 | 12/2015 | Labelle et al. |
| 10,183,934 B2 | 1/2019 | Zheng et al. |
| 2015/0284336 A1 | 10/2015 | Wang et al. |

FOREIGN PATENT DOCUMENTS

WO    2018/098401 A1    5/2018

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*

\* cited by examiner

*Primary Examiner* — Shawquia Jackson
(74) *Attorney, Agent, or Firm* — Rodney J. Fuller; Booth Udall Fuller, PLC

(57) ABSTRACT

The present invention is directed to novel aminobenzimidazole derivatives. The present invention is also directed to methods of treating a histone deacetylase (HDAC)-associated disease or inhibiting the histone deacetylating activity of a HDAC isoform in a cell or with one or more of the aminobenzimidazole derivatives.

20 Claims, 2 Drawing Sheets

AMINOBENZIMIDAZOLE DERIVATIVES, TREATMENTS, AND METHODS OF INHIBITING HISTONE DEACETYLASE

CROSS REFERENCE TO RELATED APPLICATIONS

This application is the U.S. National Stage of International Application No. PCT/US2018/049801, filed Sep. 6, 2018, which claims priority to U.S. Provisional Patent Application No. 62/554,728, filed Sep. 6, 2017, the contents of each of which are incorporated herein by reference in their entirety entireties.

TECHNICAL FIELD

The disclosure relates to aminobenzimidazole compounds, pharmaceutical compositions, use of the compounds to inhibit histone deacetylase (HDAC) and treat HDAC-associated diseases.

BACKGROUND OF THE INVENTION

Cancer is the second leading cause of death in the United States. Despite breakthroughs that have led to decreased mortality, many cancers remain refractory to treatment. Also, many cancers often develop resistance to current chemotherapies over time. The typical treatments such as chemotherapy, radiotherapy, and surgery also cause a broad spectrum of undesirable side effects. Thus, there is a need for novel compounds and methods of treating cancer and other histone deacetylase-associated diseases.

Histone deacetylases (HDACs) are a family of enzymes that deacetylate histones and non-histone proteins known to modulate gene transcription. HDACs have been associated with proliferation and differentiation of various cell types as well as pathogenesis of diseases including cancer, interstitial fibrosis, autoimmune and inflammatory diseases, and metabolic disorders.

BRIEF SUMMARY OF THE INVENTION

The present invention is directed to a compound of formula (I):

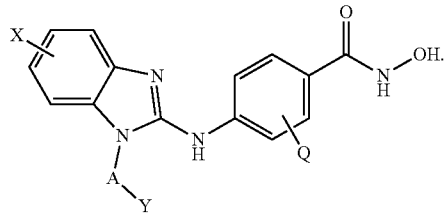

In some embodiments, X is selected from the group consisting of: H, halo, —$C_1$-$C_6$ alkyl, aryl, —$C_3$-$C_7$ cycloalkyl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; A is selected from the group consisting of: a bond, —$C_1$-$C_6$ alkyl, and —$C_3$-$C_7$ cycloalkyl, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; Y is selected from the group consisting of: H, —$C_1$-$C_6$ alkyl, —$C_3$-$C_7$ cycloalkyl, aryl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; and Q is selected from the group consisting of: —H, -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl.

In other particular embodiments, X is H or halo; A is selected from the group consisting of: a bond, —$C_1$-$C_6$ alkyl, and —$C_3$-$C_7$ cycloalkyl, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; Y is selected from the group consisting of: H, —$C_1$-$C_6$ alkyl, —$C_3$-$C_7$ cycloalkyl, aryl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; and Q is H.

In yet other embodiments, X is H or halo; A is —$C_1$-$C_6$ alkyl; Y is selected from the group consisting of: H, —$C_1$-$C_6$ alkyl, —$C_3$-$C_7$ cycloalkyl, aryl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; and Q is H.

In further embodiments, X is H or halo; A is —$C_1$-$C_6$ alkyl; Y is —$C_3$-$C_7$ cycloalkyl, unsubstituted, or substituted with one or more of: -halo and -3- to 10-membered heterocycle; and and Q is H.

In yet further embodiments, X is H or halo; A is —$C_1$-$C_3$ alkyl; Y is selected from the group consisting of: H, —$C_1$-$C_6$ alkyl, —$C_3$-$C_7$ cycloalkyl, aryl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; and Q is H.

In certain embodiments, X is H or halo; A is —$C_1$-$C_3$ alkyl; Y is —$C_3$-$C_7$ cycloalkyl, unsubstituted, or substituted with one or more of: -halo and -3- to 10-membered heterocycle; and and Q is H.

Non-limiting examples of the compound of formula (I) include:

4-((1-(cyclohexylmethyl)-1H-benzo[d]imidazol-2-yl)amino)-N-hydroxybenzamide (ID #1)

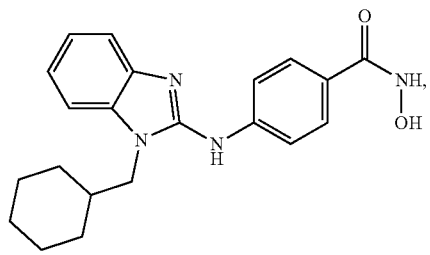 [SMILES: O=C(NO)c1ccc(Nc2nc3ccccc3n2CC2CCCCC2)cc1]

4-((1-cyclohexyl-1H-benzo[d]imidazol-2-yl)amino)-
N-hydroxybenzamide (ID #2)

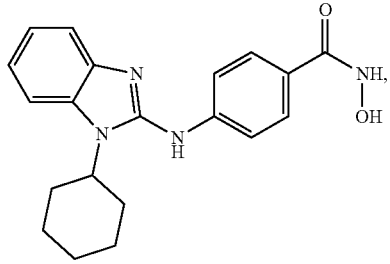 [SMILES: O=C(NO)c1ccc(Nc2nc3ccccc3n2C2CCCCC2)cc1]

4-((1-cycloheptyl-1H-benzo[d]imidazol-2-yl)
amino)-N-hydroxybenzamide (ID #3)

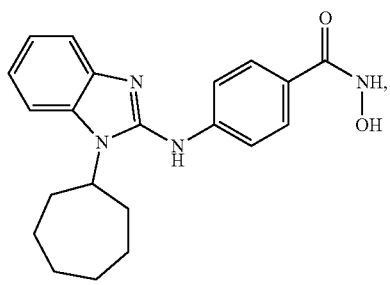 [SMILES: O=C(NO)c1ccc(Nc2nc3ccccc3n2C2CCCCCC2)cc1]

4-((1-(1-fluorocyclohexyl)methyl)-1H-benzo[d]imi-
dazol-2-yl)amino)-N-hydroxybenzamide (ID #4)

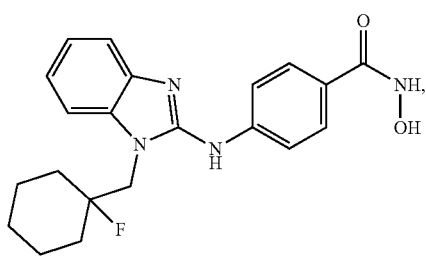 [SMILES: O=C(NO)c1ccc(Nc2nc3ccccc3n2CC2(F)CCCCC2)cc1]

4-((1-(cyclopentylmethyl)-1H-benzo[d]imidazol-2-
yl)amino)-N-hydroxybenzamide (ID #5)

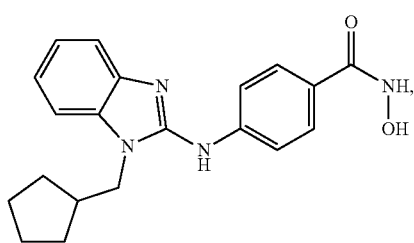 [SMILES: O=C(NO)c1ccc(Nc2nc3ccccc3n2CC2CCCC2)cc1]

4-((1-(2-cyclopentylethyl)-1H-benzo[d]imidazol-2-
yl)amino)-N-hydroxybenzamide (ID #6)

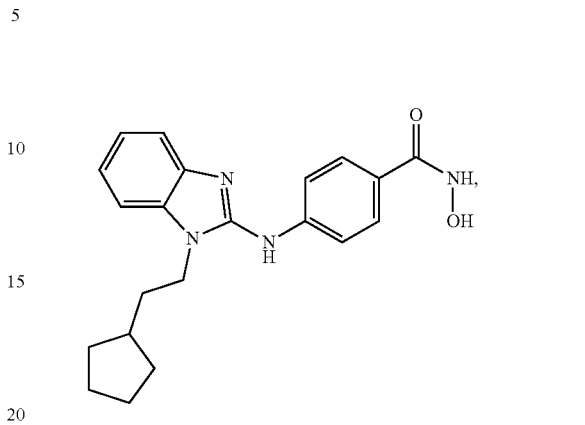

4-((1-(4,4-difluorocyclohexyl)methyl)-1H-benzo[d]
imidazol-2-yl)amino)-N-hydroxybenzamide (ID #7)

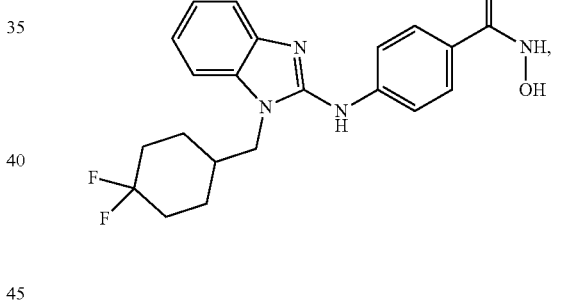

4-((1-(4,4-difluorocyclohexyl)methyl)-5-fluoro-1H-
benzo[d]imidazol-2-yl)amino)-N-hydroxybenzamide
(ID #8)

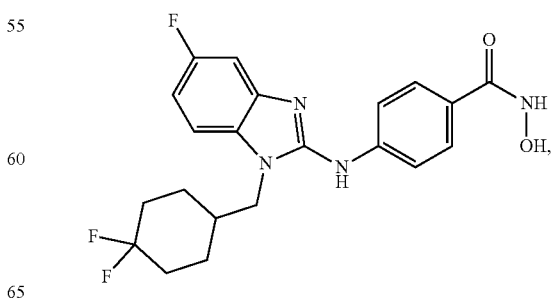

N-hydroxy-4-((1-((tetrahydro-2H-pyran-4-yl)methyl)-1H-benzo[d]imidazol-2-yl)amino)benzamide (ID #9)

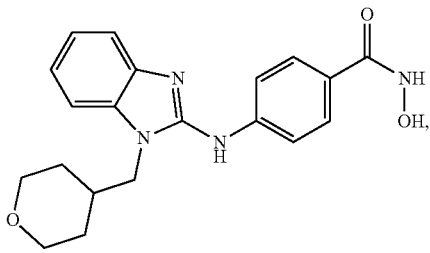 [SMILES: O=C(NO)c1ccc(Nc2nc3ccccc3n2CC2CCOCC2)cc1]

and 4-((5-fluoro-1-((tetrahydro-2H-pyran-4-yl)methyl)-1H-benzo[d]imidazol-2-yl)amino)-N-hydroxybenzamide (ID #10)

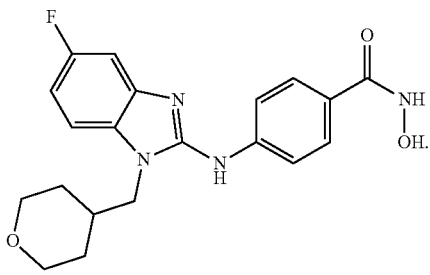 [SMILES: O=C(NO)c1ccc(Nc2nc3cc(F)ccc3n2CC2CCOCC2)cc1]

In other more specific aspects of the invention, the compound of formula (I) is 4-((1-(cyclohexylmethyl)-1H-benzo[d]imidazol-2-yl)amino)-N-hydroxybenzamide (ID #1)

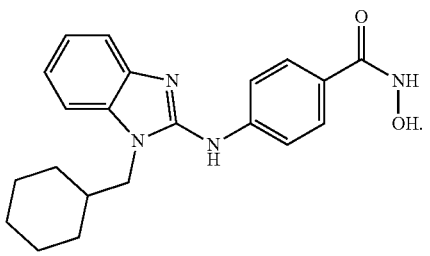 [SMILES: O=C(NO)c1ccc(Nc2nc3ccccc3n2CC2CCCCC2)cc1]

The invention is also directed to a method of inhibiting the histone deacetylating activity of a histone deacetylase (HDAC) isoform in a cell. The method typically comprises contacting the cell with the compound of formula (I), wherein the compound of formula (I) inhibits the histone deacetylating activity of the HDAC isoform in the cell. In specific embodiments, the method is used to treat a disease associated with a histone deacetylase (HDAC) isoform.

In certain embodiments, the invention is directed to a method of inhibiting an HDAC isoform in one or more various cells, for example, a cancer cell, a neuronal cell, a cell of the immune system, a cell of the circulatory system, or combinations thereof. Non-limiting examples of cancer cells include acute lymphocytic leukemia (ALL) cell, acute myeloid leukemia (AML) cell, acute promyelocytic leukemia (APL) cell, breast cancer cell, chronic myeloid leukemia (CML) cell, colon cancer cell, diffuse large B-cell lymphoma (DLBCL) cell, gastrointestinal stromal tumor (GIST) cell, glioblastoma (GBM) cell, hepatocellular carcinoma cell, Hodgkin lymphoma cell, leukemia cell, lung cancer cell, multiple myeloma cell, non-Hodgkin's lymphoma cell, non-small cell lung cancer (NSCLC) cell, neuroblastoma cell, ovarian cancer cell, pancreatic ductal adenocarcinoma cell, peripheral T-cell lymphoma cell, prostate cancer cell, uterine cancer cell, Waldenstrom myeloma cell, and combinations thereof.

Non-limiting examples of HDAC isoforms include HDAC1, HDAC3, HDAC6, and HDAC10. In one embodiment, the compound of formula (I) inhibits the histone deacetylating activity of the HDAC isoform with a half maximal inhibitory concentration ($IC_{50}$) of 0.001-10 μM, or in a more specific embodiment, 0.005-4 μM. In one aspect, the compound of formula (I) inhibits the histone deacetylating activity of the HDAC isoform by least 30%, or in a more specific aspect, 30-90%. In some aspects, the compound of formula (I) inhibits the histone deacetylating activity of the HDAC isoform, thereby inhibits cell proliferation, induces cell death, or both.

The invention is further directed to a method of treating a subject having a disease by inhibiting a histone deacetylase (HDAC) isoform. The method typically comprises administering to the subject the compound of formula (I), wherein the compound of formula (I) inhibits the histone deacetylating activity of the HDAC isoform. In some aspects, the subject is a human.

Non-limiting examples of diseases include: cell-proliferative diseases (e.g., cancer), autoimmune disorders, inflammatory disorders, neurodegenerative diseases, and combinations thereof. In some embodiments, the cell-proliferative disease is a cancer, for example, acute lymphocytic leukemia (ALL), acute myeloid leukemia (AML), acute promyelocytic leukemia (APL), breast cancer, chronic myeloid leukemia (CML), colon cancer, diffuse large B-cell lymphoma (DLBCL), gastrointestinal stromal tumor (GIST), glioblastoma (GBM), hepatocellular carcinoma, Hodgkin's lymphoma, leukemia, lung cancer, multiple myeloma, non-Hodgkin's lymphoma, non-small cell lung cancer (NSCLC), neuroblastoma, ovarian cancer, pancreatic ductal adenocarcinoma, peripheral T-cell lymphoma, prostate cancer, uterine cancer, and Waldenstrom myeloma. Non-limiting examples of autoimmune or inflammatory disorders include: airway hyperresponsiveness, Crohn's disease, inflammatory bowel disease, multiple sclerosis, psoriasis, rheumatoid arthritis, systemic lupus erythematosus, type 1 diabetes, and ulcerative colitis. Non-limiting examples of neurodegenerative disorders include: Alzheimer's disease (AD), amyotrophic lateral sclerosis (ALS), cerebral ischemia, Huntington's disease (HD), Parkinson's disease (PD), and spinal muscular atrophy.

In some aspects, the compound of formula (I) inhibits the histone deacetylating activity of the HDAC isoform, thereby inhibits proliferation, induces death, or both of certain cells. Nonlimiting examples of such cells include: cancer cells, neuronal cells, cells of the immune system, cells of the circulatory system, or combinations thereof. Non-limiting examples of cancer cells include: acute lymphocytic leukemia (ALL) cell, acute myeloid leukemia (AML) cell, acute promyelocytic leukemia (APL) cell, breast cancer cell, chronic myeloid leukemia (CML) cell, colon cancer cell, diffuse large B-cell lymphoma (DLBCL) cell, gastrointestinal stromal tumor (GIST) cell, glioblastoma (GBM) cell, hepatocellular carcinoma cell, Hodgkin lymphoma cell, leukemia cell, lung cancer cell, multiple myeloma cell, non-Hodgkin's lymphoma cell, non-small cell lung cancer (NSCLC) cell, neuroblastoma cell, ovarian cancer cell, pancreatic ductal adenocarcinoma cell, peripheral T-cell lymphoma cell, prostate cancer cell, uterine cancer cell, Waldenstrom myeloma cell, and combinations thereof.

In some aspects, the compound of formula (I) is in a pharmaceutically acceptable carrier. In one embodiment, the composition is administered systemically. In another embodiment, the composition is administered locally. In yet another embodiment, the composition is administered orally or intravenously. In one embodiment, the composition is administered about every 6, 8, 12, 16, 20, or 24 hours. In one embodiment, the compound of formula (I) is administered at 10-400 mg/kg, or in a more specific embodiment, at 40-250 mg/kg.

Non-limiting examples of HDAC isoforms include: HDAC1, HDAC3, HDAC6, and HDAC10. In one embodiment, the compound of formula (I) inhibits the histone deacetylating activity of the HDAC isoform with a half maximal inhibitory concentration ($IC_{50}$) of 0.001-10 µM, or in a more specific embodiment, 0.005-4 µM. In one aspect, the compound of formula (I) inhibits the histone deacetylating activity of the HDAC isoform by least 30%, or in a more specific aspect, 30-90%.

In some aspects, the subject is further administered a chemotherapy drug. Non-limiting examples of chemotherapy drugs include: pomalidomide, dexamethasone, and a combination thereof.

The invention is further directed to a method of treating a histone deacetylase (HDAC)-associated disease in a subject. The method typically comprises administering to the subject the compound of formula (I). In some embodiments, the compound of formula (I) is administered in a therapeutically effective amount. In some aspects, the subject is a human.

Non-limiting examples of HDAC-associated diseases include: cell-proliferative diseases (e.g., cancer), autoimmune disorders, inflammatory disorders, neurodegenerative diseases, and combinations thereof. In some embodiments, the cell-proliferative disease is a cancer, for example, acute lymphocytic leukemia (ALL), acute myeloid leukemia (AML), acute promyelocytic leukemia (APL), breast cancer, chronic myeloid leukemia (CML), colon cancer, diffuse large B-cell lymphoma (DLBCL), gastrointestinal stromal tumor (GIST), glioblastoma (GBM), hepatocellular carcinoma, Hodgkin's lymphoma, leukemia, lung cancer, multiple myeloma, non-Hodgkin's lymphoma, non-small cell lung cancer (NSCLC), neuroblastoma, ovarian cancer, pancreatic ductal adenocarcinoma, peripheral T-cell lymphoma, prostate cancer, uterine cancer, and Waldenstrom myeloma. Non-limiting examples of autoimmune or inflammatory disorders include: airway hyperresponsiveness, Crohn's disease, inflammatory bowel disease, multiple sclerosis, psoriasis, rheumatoid arthritis, systemic lupus erythematosus, type 1 diabetes, and ulcerative colitis. Non-limiting examples of neurodegenerative disorders include: Alzheimer's disease (AD), amyotrophic lateral sclerosis (ALS), cerebral ischemia, Huntington's disease (HD), Parkinson's disease (PD), and spinal muscular atrophy.

In some aspects, the compound of formula (I) is in a pharmaceutically acceptable carrier. In one embodiment, the composition is administered systemically. In another embodiment, the composition is administered locally. In yet another embodiment, the composition is administered orally or intravenously. In one embodiment, the composition is administered about every 6, 8, 12, 16, 20, or 24 hours. In one embodiment, the compound of formula (I) is administered at 10-400 mg/kg, or in a more specific embodiment, at 40-250 mg/kg. In some aspects, the subject is further administered a chemotherapy drug. Non-limiting examples of chemotherapy drugs include: pomalidomide, dexamethasone, and a combination thereof.

In some aspects, the disease is associated with HDAC1, HDAC3, HDAC6, HDAC10, or combinations thereof. In one embodiment, the compound of formula (I) inhibits the histone deacetylating activity of the HDAC isoform associated with the disease with a half maximal inhibitory concentration ($IC_{50}$) of 0.001-10 µM, or in a more specific embodiment, 0.005-4 µM. In one aspect, the compound of formula (I) inhibits the histone deacetylating activity of the HDAC isoform associated with the disease by least 30%, or in a more specific aspect, 30-90%.

DETAILED DESCRIPTION OF THE INVENTION

Figure 1:
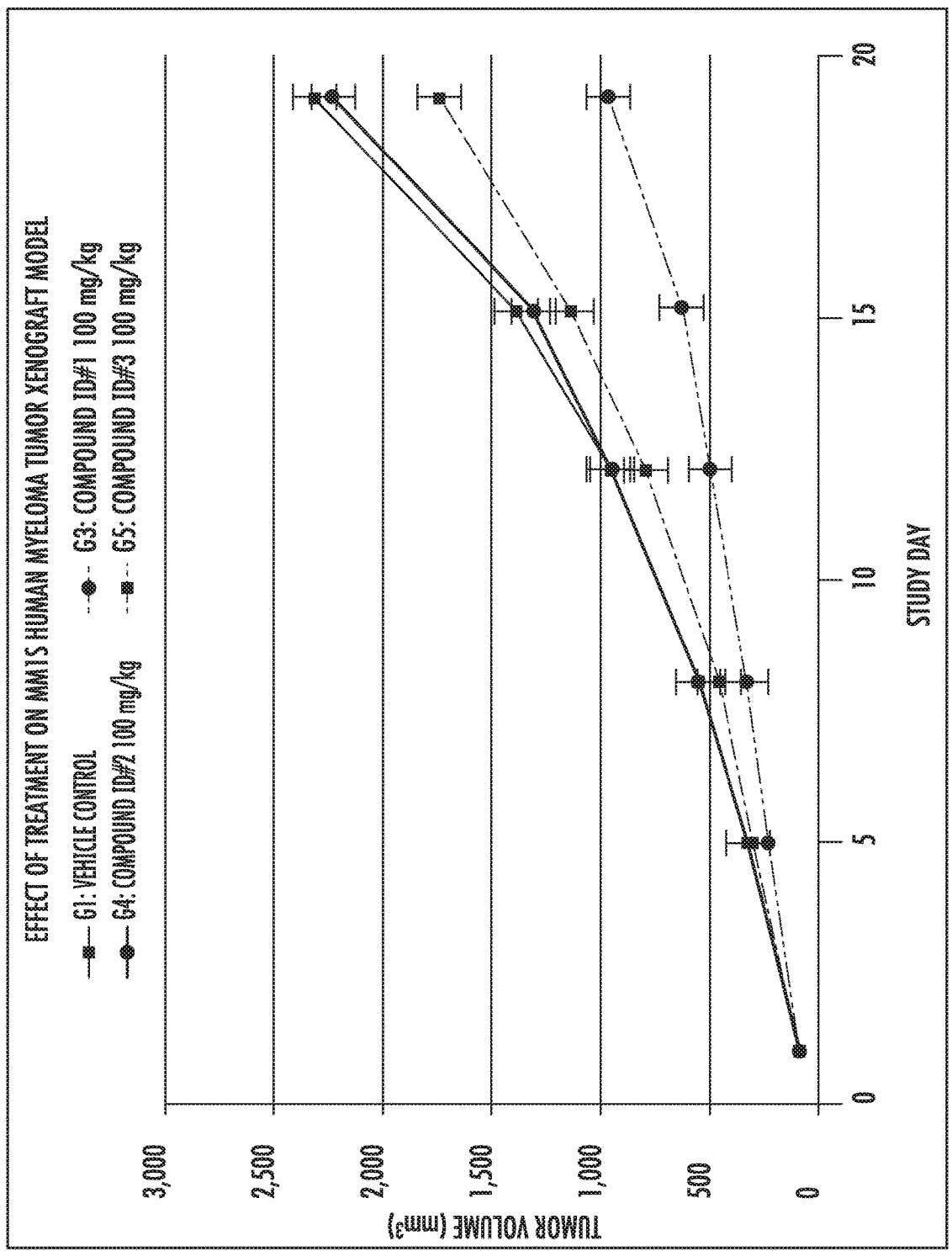
FIG. 1 depicts the effect of treatment with Compound ID #1, Compound ID #2, or Compound ID #3 on tumor volume in a human myeloma tumor xenograft model.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices, compositions, and technologies to which the disclosed invention may be applied. The full scope of the inventions is not limited to the examples that are described below.

Compounds of Formula (I)

Herein the inventors disclose a compound of formula (I):

A compound of formula (I):

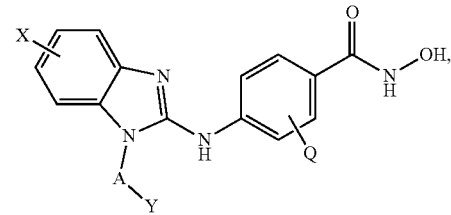

wherein:
X is selected from the group consisting of: H, halo, —$C_1$-$C_6$ alkyl, aryl, —$C_3$-$C_7$ cycloalkyl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —C$_1$-C$_6$ alkyl;

A is selected from the group consisting of: a bond, —C$_1$-C$_6$ alkyl, and —C$_3$-C$_7$ cycloalkyl, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl;

Y is selected from the group consisting of: H, —C$_1$-C$_6$ alkyl, —C$_3$-C$_7$ cycloalkyl, aryl, and -3- to 10-membered heterocycle, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; and Q is selected from the group consisting of: —H, -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl.

In some embodiments, X is H or halo. In other embodiments, Q is H. In yet other embodiments, A is —C$_1$-C$_6$ alkyl. In further embodiments, A is —C$_1$-C$_3$ alkyl. In yet further embodiments, Y is —C$_3$-C$_7$ cycloalkyl, unsubstituted, or substituted with one or more of: -halo and -3- to 10-membered heterocycle.

In some aspects, X is H or halo; A is selected from the group consisting of: a bond, —C$_1$-C$_6$ alkyl, and —C$_3$-C$_7$ cycloalkyl, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; Y is selected from the group consisting of: H, —C$_1$-C$_6$ alkyl, —C$_3$-C$_7$ cycloalkyl, aryl, and -3- to 10-membered heterocycle, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; and Q is —H in the compound of formula (I).

In other aspects, X is H or halo; A is —C$_1$-C$_6$ alkyl; Y is selected from the group consisting of: H, —C$_1$-C$_6$ alkyl, —C$_3$-C$_7$ cycloalkyl, aryl, and -3- to 10-membered heterocycle, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; and Q is —H in the compound of formula (I).

In yet other aspects, X is H or halo; A is —C$_1$-C$_3$ alkyl; Y is selected from the group consisting of: H, —C$_1$-C$_6$ alkyl, —C$_3$-C$_7$ cycloalkyl, aryl, and -3- to 10-membered heterocycle, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; and Q is —H in the compound of formula (I).

In further aspects, X is H or halo; A is selected from the group consisting of: a bond, —C$_1$-C$_6$ alkyl, and —C$_3$-C$_7$ cycloalkyl, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; Y is —C$_3$-C$_7$ cycloalkyl or —C$_3$-C$_7$ cycloalkyl substituted with one or more of: -halo and -3- to 10-membered heterocycle; and Q is —H in the compound of formula (I).

In yet further aspects, X is H or halo; A is —C$_1$-C$_6$ alkyl; Y is —C$_3$-C$_7$ cycloalkyl or —C$_3$-C$_7$ cycloalkyl substituted with one or more of: -halo and -3- to 10-membered heterocycle; and Q is —H in the compound of formula (I).

In certain aspects, X is H or halo; A is —C$_1$-C$_3$ alkyl; Y is —C$_3$-C$_7$ cycloalkyl or —C$_3$-C$_7$ cycloalkyl substituted with one or more of: -halo and -3- to 10-membered heterocycle; and Q is —H in the compound of formula (I).

Non-limiting examples of compound of formula (I) include:

4-((1-(cyclohexylmethyl)-1H-benzo[d]imidazol-2-yl)amino)-N-hydroxybenzamide (ID #1)

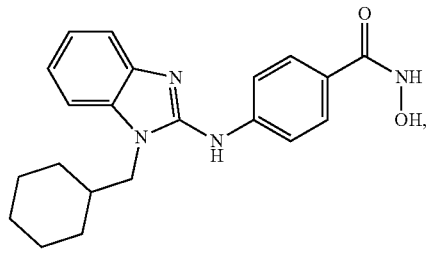 [SMILES: O=C(NO)c1ccc(Nc2nc3ccccc3n2CC2CCCCC2)cc1]

4-((1-cyclohexyl-1H-benzo[d]imidazol-2-yl)amino)-N-hydroxybenzamide (ID #2)

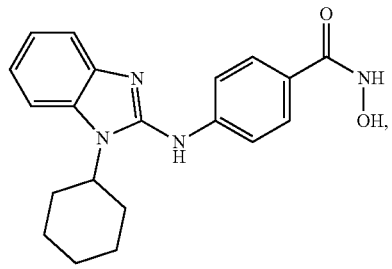 [SMILES: O=C(NO)c1ccc(Nc2nc3ccccc3n2C2CCCCC2)cc1]

4-((1-cycloheptyl-1H-benzo[d]imidazol-2-yl)amino)-N-hydroxybenzamide (ID #3)

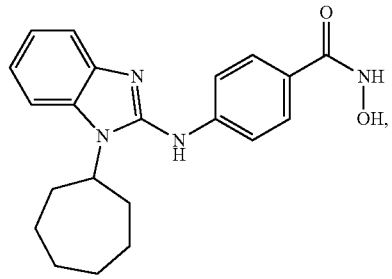 [SMILES: O=C(NO)c1ccc(Nc2nc3ccccc3n2C2CCCCCC2)cc1]

4-((1-(1-fluorocyclohexyl)methyl)-1H-benzo[d]imidazol-2-yl)amino)-N-hydroxybenzamide (ID #4)

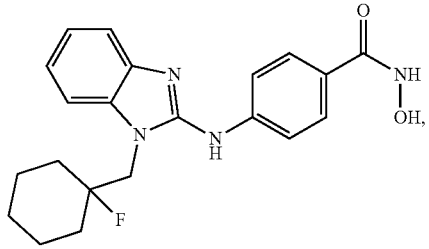 [SMILES: O=C(NO)c1ccc(Nc2nc3ccccc3n2CC2(F)CCCCC2)cc1]

4-((1-(cyclopentylmethyl)-1H-benzo[d]imidazol-2-yl)amino)-N-hydroxybenzamide (ID #5)

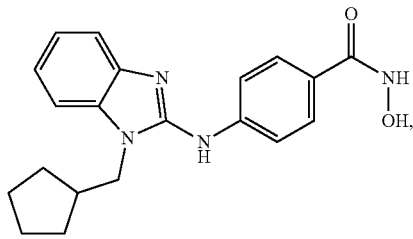 [SMILES: O=C(NO)c1ccc(Nc2nc3ccccc3n2CC2CCCC2)cc1]

4-((1-(2-cyclopentylethyl)-1H-benzo[d]imidazol-2-yl)amino)-N-hydroxybenzamide (ID #6)

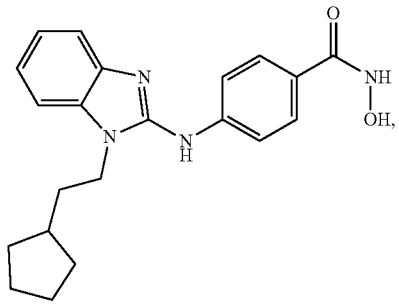 [SMILES: O=C(NO)c1ccc(Nc2nc3ccccc3n2CCC2CCCC2)cc1]

4-((1-((4,4-difluorocyclohexyl)methyl)-1H-benzo[d]imidazol-2-yl)amino)-N-hydroxybenzamide (ID #7)

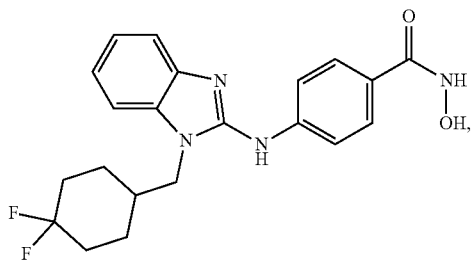 [SMILES: O=C(NO)c1ccc(Nc2nc3ccccc3n2CC2CCC(F)(F)CC2)cc1]

4-((1-(4,4-difluorocyclohexyl)methyl)-5-fluoro-1H-benzo[d]imidazol-2-yl)amino)-N-hydroxybenzamide (ID #8)

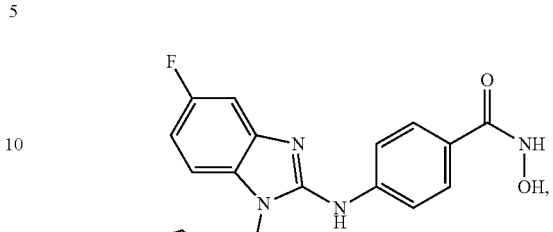

N-hydroxy-4-((1-((tetrahydro-2H-pyran-4-yl)methyl)-1H-benzo[d]imidazol-2-yl)amino)benzamide (ID #9)

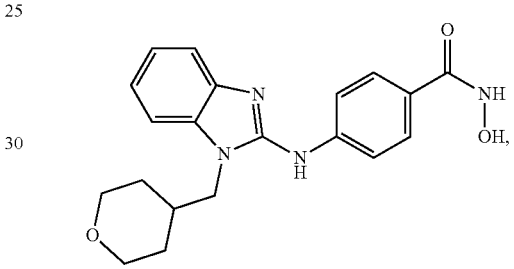

and 4-((5-fluoro-1-((tetrahydro-2H-pyran-4-yl)methyl)-1H-benzo[d]imidazol-2-yl)amino)-N-hydroxybenzamide (ID #10)

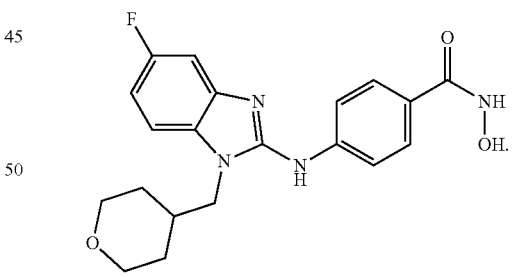

In some embodiments, the compound is selected from the group consisting of: 4-((1-(cyclohexylmethyl)-1H-benzo[d]imidazol-2-yl)amino)-N-hydroxybenzamide (ID #1), 4-((1-(1-fluorocyclohexyl)methyl)-1H-benzo[d]imidazol-2-yl)amino)-N-hydroxybenzamide (ID #4), 4-((1-(cyclopentylmethyl)-1H-benzo[d]imidazol-2-yl)amino)-N-hydroxybenzamide (ID #5), 4-((1-(2-cyclopentylethyl)-1H-benzo[d]imidazol-2-yl)amino)-N-hydroxybenzamide (ID #6), 4-((1-((4,4-difluorocyclohexyl)methyl)-1H-benzo[d]imidazol-2-yl)amino)-N-hydroxybenzamide (ID #7), 4-((1-(4,4-difluorocyclohexyl)methyl)-5-fluoro-1H-benzo[d]imidazol-2-yl)amino)-N-hydroxybenzamide (ID #8), N-hydroxy-4-((1-((tetrahydro-2H-pyran-4-yl)methyl)-1H-benzo[d]imidazol-2-yl)amino)benzamide (ID #9), and 4-((5-fluoro-1-((tetrahydro-2H-pyran-4-yl)methyl)-1H-benzo[d]imidazol-2-yl)amino)-N-hydroxybenzamide (ID #10).

In other embodiments, the compound of formula (I) is 4-((1-(cyclohexylmethyl)-1H-benzo[d]imidazol-2-yl)amino)-N-hydroxybenzamide (ID #1)

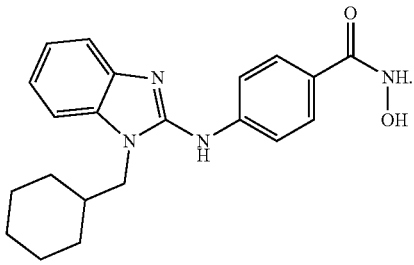 [SMILES: O=C(NO)c1ccc(Nc2nc3ccccc3n2CC2CCCCC2)cc1]

A —$C_1$-$C_6$ alkyl includes any straight or branched, saturated or unsaturated, substituted or unsubstituted hydrocarbon comprised of between one and six carbon atoms. Non-limiting examples of —$C_1$-$C_6$ alkyl include: methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl, and 3-hexynyl, etc. Non-limiting examples of substituting groups include: halo, —$C_1$-$C_6$ alkyl, —O—($C_1$-$C_6$ alkyl), —OH, —CN, —COOR', —OC(O)R', —NHR', and N(R')$_2$, —NHC(O)R', and —C(O)NHR', wherein R' is —H or —$C_1$-$C_6$ alkyl.

An aryl includes any unsubstituted or substituted phenyl or napthyl. Non-limiting examples of substituting groups include: halo, —$C_1$-$C_6$ alkyl, —O—($C_1$-$C_6$ alkyl), —OH, —CN, —COOR', —OC(O)R', NHR', N(R')$_2$, —NHC(O), R', and —C(O)NEtR', wherein R' is —H or —$C_1$-$C_6$ alkyl.

A $C_3$-$C_7$ cycloalkyl includes any 3-, 4-, 5-, 6-, or 7-membered substituted or unsubstituted non-aromatic carbocyclic ring. Non-limiting examples of $C_3$-$C_7$ cycloalkyl include: cyclopropyl, cyclobutyl, cyclopentyl, cyclopentadienyl, cyclohexyl, cyclohexenyl, cycloheptyl, cycloheptanyl, 1,3-cyclohexadienyl, 1,4-cyclohexadienyl, 1,3-cycloheptadienyl, and 1,3,5-cycloheptatrienyl. Non-limiting examples of substituting groups include: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or unsubstituted —$C_1$-$C_6$ alkyl.

A halo includes any halogen, non-limiting examples include: —F, —Cl, —Br, and —I.

A heterocycle is an optionally substituted, saturated, unsaturated, or aromatic cyclic moiety, wherein the cyclic moiety is interrupted by at least one heteroatom selected from the group consisting of: oxygen (O), sulfur (S), and nitrogen (N). A heterocycle is a monocyclic or polycyclic ring. A suitable substituents is selected from the group consisting of: (1) halogen, halogenated —$C_1$-$C_6$ alkyl, halogenated —$C_1$-$C_6$ alkoxy, amino, amidino, amido, azido, cyano, guanidino, hydroxyl, nitro, nitroso, and urea; (2) OS(O)$_2$R, OS(O)$_2$OR, S(O)$_2$OR S(O)$_{0-2}$R, and C(O)OR, wherein R is H, $C_1$-$C_6$ alkyl, aryl or 3- to 10-membered heterocycle; (3) OP(O)OR$_1$OR$_2$, P(O)OR$_1$OR$_2$, SO$_2$NR$_1$R$_2$, NR$_1$SO$_2$R$_2$, C(R$_1$)NR$_2$, and C(R$_1$)NOR$_2$, wherein R$_1$ and R$_2$ is independently H, $C_1$-$C_6$ alkyl, aryl, or 3- to 10-membered heterocycle; and (4) NR$_1$C(O)R$_2$, NR$_1$C(O)OR$_2$, NR$_3$C(O)NR$_2$R$_1$, C(O)NR$_1$R$_2$, and OC(O)NR$_1$R$_2$, wherein R$_1$, R$_2$ and R$_3$ are each independently selected from the group consisting of: H, $C_1$-$C_6$ alkyl, aryl, and 3- to 10-membered heterocycle, or R$_1$ and R$_2$ are taken together with the atoms to which they are attached to form a 3- to 10-membered heterocycle.

Non-limiting examples of the substituent of the heterocycle include: halogen (Br, Cl, I, or F), cyano, nitro, oxo, amino, $C_{1-4}$ alkyl (e.g., CH$_3$, C$_2$H$_5$, or isopropyl), $C_{1-4}$ alkoxy (e.g., OCH$_3$ or OC$_2$H$_5$), halogenated $C_{1-4}$ alkyl (e.g., CF$_3$ or CHF$_2$), halogenated $C_{1-4}$ alkoxy (e.g., OCF$_3$ or OC$_2$F$_5$), COOH, COO—$C_{1-4}$ alkyl, CO—$C_{1-4}$ alkyl, $C_{1-4}$ alkyl —S— (e.g., CH$_3$S or C$_2$H$_5$S), halogenated $C_{1-4}$ alkyl —S— (e.g., CF$_3$S or C$_2$F$_5$S), benzyloxy, and pyrazolyl.

Non-limiting examples of heterocycles include: azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl, and pyridopyrimidinyl.

In some embodiments, the disclosed compound and its intermediates exist in different tautomeric forms. Tautomers include any structural isomers of different energies that have a low energy barrier to interconversion. One example is proton tautomers (prototropic tautomers). In this example, the interconversions occur via the migration of a proton. Non-limiting examples of prototropic tautomers include keto-enol and imine-enamine isomerizations. In other embodiments (illustrated graphically below), proton migrates between the 1-position and 3-position nitrogen atoms of the benzimidazole ring. As a result, Formulas Ia and Ib are tautomeric forms of each other:

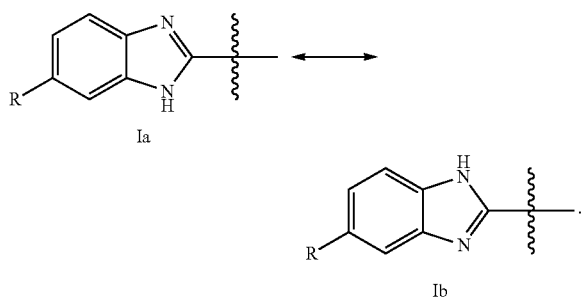

The invention encompasses any other physiochemical or stereochemical form that the disclosed compound may assume. Such form includes diastereomers, racemates, isolated enantiomers, hydrated forms, solvated forms, or any other known or yet to be disclosed crystalline, polymorphic crystalline, or amorphous form. Amorphous forms lack a distinguishable crystal lattice and therefore lack an orderly arrangement of structural units. Many pharmaceutical compounds have amorphous forms. Methods of generating such chemical forms will be well known by one with skill in the art.

In some aspects of the invention the disclosed compound is in the form of a pharmaceutically acceptable salt. Pharmaceutically acceptable salts include any salt derived from an organic or inorganic acid. Non-limiting examples of such salts include: salts of hydrobromic acid, hydrochloric acid, nitric acid, phosphoric acid, and sulphuric acid. Non-limiting examples of the organic acid addition salt include: salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid, and any other acid now known or yet to be disclosed. It will be appreciated by one skilled in the art that such pharmaceutically acceptable salts may be used in the formulation of a pharmacological composition. Such salts may be prepared by reacting the disclosed compound with a suitable acid in a manner known by those skilled in the art.

The invention further encompasses aspects in which a protecting group is added to the compound. One skilled in the art would recognize that during the synthesis of complex molecules, one group on the disclosed compound may happen to interfere with an intended reaction that includes a second group on the compound. Temporarily masking or protecting the first group encourages the desired reaction. Protection involves introducing a protecting group to a group to be protected, carrying out the desired reaction, and removing the protecting group Removal of the protecting group may be referred to as deprotection. Examples of compounds to be protected in some syntheses include: hydroxy groups, amine groups, carbonyl groups, carboxyl groups, and thiols.

Many protective groups and reagents capable of introducing them into synthetic processes have been and are continuing to be developed today. A protecting group may result from any chemical synthesis that selectively attaches a group that is resistant to certain reagents to the chemical group to be protected without significant effects on any other chemical groups in the molecule, remains stable throughout the synthesis, and may be removed through conditions that do not adversely react with the protected group, nor any other chemical group in the molecule. Multiple protecting groups may be added throughout a synthesis and one skilled in the art would be able to develop a strategy for specific addition and removal of the protecting groups to and from the groups to be protected.

Protecting groups, reagents that add those groups, preparations of those reagents, protection and deprotection strategies under a variety of conditions, including complex syntheses with mutually complementary protecting groups are all well known in the art. Nonlimiting examples of all of these may be found in Green et al, *Protective Groups in Organic Chemistry* $2^{nd}$ Ed., (Wiley 1991), and Harrison et al, *Compendium of Synthetic Organic Methods*, Vols. 1-8 (Wiley, 1971-1996) both of which hereby incorporated by reference in its entirety.

Racemates, individual enantiomers, or diasteromers of the disclosed compound may be prepared by specific synthesis or resolution through any method now known or yet to be disclosed. For example, the disclosed compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

Pharmaceutical Compositions Comprising the Compound of Formula (I)

The invention further encompasses pharmaceutical compositions that comprise any one of the disclosed compounds of formula (I) as an ingredient.

Such pharmaceutical compositions may take any physical form necessary depending on a number of factors including the desired method of administration and the physicochemical and stereochemical form taken by the disclosed compound or pharmaceutically acceptable salts of the compound. Such physical forms include a solid, liquid, gas, sol, gel, aerosol, or any other physical form now known or yet to be disclosed. The concept of a pharmaceutical composition including the disclosed compound also encompasses the disclosed compound or a pharmaceutically acceptable salt thereof without any other additive. The physical form of the invention may affect the route of administration and one skilled in the art would know to choose a route of administration that takes into consideration both the physical form of the compound and the disorder to be treated. Pharmaceutical compositions that include one of the disclosed compounds may be prepared using methodology well known in the pharmaceutical art. A pharmaceutical composition that includes one of the disclosed compounds may include a second effective compound of a distinct chemical formula from the disclosed compound. This second effective compound may have the same or a similar molecular target as the target or it may act upstream or downstream of the molecular target of the disclosed compound with regard to one or more biochemical pathways.

Pharmaceutical compositions including one of the disclosed compounds include materials capable of modifying the physical form of a dosage unit. In one nonlimiting example, the composition includes a material that forms a coating that holds in the compound. Materials that may be used in such a coating include, for example, sugar, shellac, gelatin, or any other inert coating agent.

Pharmaceutical compositions including one of the disclosed compounds may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single-phase, bi-phasic, or tri-phasic systems.

In some aspects of the invention, the pharmaceutical composition one of the disclosed compounds is in the form of a solvate. Such solvates are produced by the dissolution of the disclosed compound in a pharmaceutically acceptable solvent. Pharmaceutically acceptable solvents include any mixtures of more than one solvent. Such solvents may include: pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include one of the disclosed compounds may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable, or synthetic oils). Such carriers include particulates such as a tablet or powder, liquids such as an oral syrup or injectable liquid and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include: polyethylene glycol, cyclodextrin, oils, or any other similar liquid carrier that may be formulated into a capsule. Still further examples of carriers include: sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including one of the disclosed compounds may take any of a number of formulations depending on the physicochemical form of the composition and the type of administration. Such forms include: solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Pharmaceutical compositions including one of the disclosed compounds may be prepared in a form that facilitates topical or transdermal administration. Such preparations may be in the form of a solution, emulsion, ointment, gel base, transdermal patch or iontophoresis device. Examples of bases used in such compositions include: petrolatum, lanolin, polyethylene glycols, beeswax, mineral oil, diluents such as water and alcohol, and emulsifiers and stabilizers, thickening agents, or any other suitable base now known or yet to be disclosed.

HDAC and Associated Diseases

Histone acetyltransferases (HAT) impact gene expression by controlling the coiling and uncoiling of DNA around histones. Histone acetyltransferases accomplish this by acetylating lysine residues in core histones leading to less compact and more transcriptionally active chromatin. In contrast, histone deacetylases (HDAC) remove the acetyl groups from lysine residues, leading to a more condensed and transcriptionally silenced chromatin. Reversible modification of the terminal tails of core histones constitutes the major epigenetic mechanism for remodeling of higher-order chromatin structure and controlling gene expression. HDAC inhibitors (HDI) block this action and can result in hyper-acetylation of histones, thereby affecting gene expression. Thagalingam S., Cheng K H, Lee H J et al., *Ann. N.Y. Acad. Sci.* 983: 84-100, 2003; Marks P A. Richon V M, Rifkind R A, *J. Natl. Cancer Inst.* 92 (15) 1210-16, 2000; Dokmanovic M, Clarke C., Marks P A, *Mol. Cancer Res.* 5 (10) 981-989, 2007.

Histone deacetylase (HDAC) inhibitors are a new class of cytostatic agents that inhibit the proliferation of tumor cells in culture and in vivo by inducing cell cycle arrest, differentiation and/or apoptosis. Acetylation and deacetylation play important roles in the modulation of chromatin topology and the regulation of gene transcription. Histone deacetylase inhibitors induce the accumulation of hyper-acetylated nucleosome core histones in many regions of chromatin but affect the expression of only a small subset of genes, leading to transcriptional activation of some genes, but repression of an equal or larger number of other genes. Non-histone proteins such as transcription factors are also targets for acetylation with varying functional effects. Acetylation enhances the activity of some transcription factors such as the tumor suppressor p53 and the erythroid differentiation factor GATA-1 but may repress the transcriptional activity of others including T cell factor and the co-activator ACTR. Recent studies have shown that the estrogen receptor alpha (ERalpha) can be hyperacetylated in response to histone deacetylase inhibition, suppressing ligand sensitivity and regulating transcriptional activation by histone deacetylase inhibitors. Conservation of the acetylated ERalpha motif in other nuclear receptors suggests that acetylation may play an important regulatory role in diverse nuclear receptor signaling functions. A number of structurally diverse histone deacetylase inhibitors have shown potent antitumor efficacy with little toxicity in vivo in animal models. Several compounds are currently in early phase clinical development as potential treatments for solid and hematological cancers both as monotherapy and in combination with cytotoxics and differentiation agents.

The HDAC enzyme family constitutes a family of 18 genes that can be grouped into four subclasses; classes I-IV, based on their homology to respective yeast orthologs. HDACs, belonging to classes I, II and IV, comprise 11 members, namely HDAC isoforms 1-11, commonly referred to as the classical HDACs, are metal-dependent hydrolases. HDACs of class III, which comprise 7 members, known as sirtuins, namely Sirt 1-7, are NAD+-dependent hydrolases. Class I HDACs are nuclear proteins with ubiquitous tissue expression. Class II and IV HDACs are found in both the nucleus and cytoplasm and exhibit tissue-specific expression. The Class II HDAC family is further subdivided into subclasses IIA and IIB. Class IIA comprises isoforms HDAC4, HDAC5, HDAC7 and HDAC9 while Class IIB comprises isoforms HDAC6 and HDAC10. HDAC6 contains two tandem deacetylase domains and a C-terminal zinc finger domain. HDAC10 is structurally related to HDAC6 but has one additional catalytic domain. Table 1 represents the cellular location and tissue expression of classical HDACs (adapted from Witt, O. et al., Cancer Lett., 277:8-21 (2008)).

TABLE 1

Classical HDACs, Cellular Location and Tissue Expression

| Class | Isoform | Cellular Location | Tissue Expression |
| --- | --- | --- | --- |
| Class I | HDAC 1 | Nuclear | Ubiquitous |
|  | HDAC2 | Nuclear | Ubiquitous |
|  | HDAC3 | Nuclear | Ubiquitous |
|  | HDAC8 | Nuclear/cytoplasmic | Ubiquitous |
| Class II A | HDAC4 | Nuclear/cytoplasmic | Heart, smooth muscles, brain |
|  | HDAC5 | Nuclear/cytoplasmic | Heart, smooth muscle, brain |
|  | HDAC7 | Nuclear/cytoplasmic | Heart, placenta, pancreas, smooth muscle |
|  | HDAC9 | Nuclear/cytoplasmic | Smooth muscle, brain |
| Class II B | HDAC6 | Cytoplasmic | Kidney, liver, heart, pancreas |
|  | HDAC10 | Cytoplasmic | Spleen, kidney, liver |
| Class IV | HDAC11 | Nuclear/cytoplasmic | Heart, smooth muscle, kidney, brain |

HDACs play a significant role in both normal and aberrant cell proliferation and differentiation. HDACs have been associated with some disease states involving proliferation, including, but not limited to, cell proliferative diseases and conditions, such as various forms of cancer. (Reviewed in Witt, O. et al., Cancer Lett., 277:8-21 (2008); and Portella A. et al., Nat. Biotechnol., 28:1057-1068 (2010)). Class I and II HDACs have been identified as attractive targets for anticancer therapy. In particular, distinct class I and class II HDAC proteins are overexpressed in some cancers, including ovarian (HDAC1-3), gastric (HDAC2), and lung cancers (HDAC1 and 3), among others. Also, a possible correlation between HDAC8 and acute myeloid leukemia (AML) has been suggested. Concerning class II HDAC proteins, aberrant expression of HDAC6 is induced in some breast cancer cells. Based on their clinical effects, HDAC inhibitors have been identified that suppress tumor cell proliferation, induce cell differentiation, and upregulate crucial genes associated with anti-cancer effects. HDACs have also been implicated in various types of cancers (Bali P, et al., "Inhibition of histone deacetylase 6 acetylates and disrupts the chaperone function of heat shock protein 90: A novel basis for antileukemia activity of histone deacetylase inhibitors," J. Biol. Chem., 2005 280:26729-26734; Santo L. et al., "Preclinical activity, pharmacodynamic and pharmacokinetic properties of a selective HDAC6 inhibitor, ACY-1215, in combination with bortezomib in multiple myeloma," Blood, 2012, 119 (11): 2579-89), autoimmune or inflammatory diseases (Shuttleworth, S. J., et al., Curr. Drug Targets, 11:1430-1438 (2010)), cognitive and neurodegenerative diseases (Fischer, A., et al., Trends Pharmacol. Sci., 31:605-617 (2010); Chuang, D.-M., et al., Trends Neurosci. 32:591-601 (2009)), fibrotic diseases (Pang, M. et al., J. Pharmacol. Exp. Ther., 335:266-272 (2010)), protozoal diseases (see, e.g., U.S. Pat. No. 5,922,837), and viral diseases (Margolis, D. M. et al., Curr. Opin. HIV AIDS, 6:25-29 (2011)).

In recent years, there has been an effort to develop HDAC inhibitors as cancer treatments and/or as an adjunct therapy. Mark P A. et al. *Expert Opinion on Investigational Drugs* 14 (12): 1497-1511 (2005). The exact mechanisms by which the compounds may work are unclear, but epigenetic pathways have been studied to help elucidate the exact biological pathways. Claude Monneret, *Anticancer Drugs* 18(4):363-370 2007. For example, HDAC inhibitors have been shown to induce p21 (WAFT) expression, a regulator of p53's tumor suppressor activity. Rochon V M. et al., *Proc. Natl. Acad. Sci. U.S.A.* 97(18): 10014-10019, 2000. HDACs are involved in the pathway by which the retinoblastoma protein (pRb) suppresses cell proliferation. The pRb protein is part of a complex that attracts HDACs to the chromatin so that it will deacetylate histones. Brehm A. et al., *Nature* 391 (6667): 597-601, 1998. HDAC1 negatively regulates the cardiovascular transcription factor Kruppel-like factor 5 through direct interaction. Matsumura T. et al., *J. Biol. Chem.* 280 (13): 12123-12129, 2005. Estrogen is well-established as a mitogenic factor implicated in the tumorigenesis and progression of breast cancer via its binding to the estrogen receptor alpha (ERα). Recent data indicate that chromatin inactivation mediated by HDAC and DNA methylation is a critical component of ERα silencing its human breast cancer cells. Zhang Z. et al., *Breast Cancer Res. Treat.* 94(1): 11-16, 2005.

Methods of Inhibiting a HDAC Isoform in a Cell

The method comprising contacting the cell with an effective amount of any one of the disclosed compounds of formula (I), or a pharmaceutically acceptable salt form thereof.

In some embodiments, the cell is selected from the group consisting of: a cancer cell, a neuronal cell, a cell of the immune system, a cell of the circulatory system, and combinations thereof. In other embodiments, the cell is a cancer cell. In yet other embodiments, the cell is a neuronal cell. In further embodiments, the cell is a cell of the immune system. In yet further combinations, the cell is a cell of the circulatory system.

Non-limiting examples of the cancer cell include: an acute lymphocytic leukemia (ALL) cell, an acute myeloid leukemia (AML) cell, an acute promyelocytic leukemia (APL) cell, a breast cancer cell, a chronic myeloid leukemia (CML) cell, a colon cancer cell, a diffuse large B-cell lymphoma (DLBCL) cell, a gastrointestinal stromal tumor (GIST) cell, a glioblastoma (GBM) cell, a hepatocellular carcinoma cell, a Hodgkin lymphoma cell, a leukemia cell, a lung cancer cell, a multiple myeloma cell, a non-Hodgkin's lymphoma cell, a non-small cell lung cancer (NSCLC) cell, a neuroblastoma cell, an ovarian cancer cell, a pancreatic ductal adenocarcinoma cell, a peripheral T-cell lymphoma cell, a prostate cancer cell, a uterine cancer cell, and a Waldenstrom myeloma cell, etc.

In some embodiments, the HDAC isoform is selected from the group consisting of: HDAC1, HDAC2, HDAC3, HDAC4, HDAC5, HDAC6, HDAC7, HDAC8, HDAC9, HDAC10, HDAC11, and combinations thereof. In other embodiments, the HDAC isoform is selected from the group consisting of: HDAC1, HDAC3, HDAC6, HDAC10, and combinations thereof.

In some aspects, the compound of formula (I) inhibits the histone deacetylating activity of the HDAC isoform with a half maximal inhibitory concentration ($IC_{50}$) of 0.001-4 µM, or any number range in between, e.g., 0.001-3.5 µM, 0.002-

3.5 µM, 0.002-3 µM, 0.003-3 µM, 0.003-2.5 µM, 0.005-2.5 µM, 0.005-2 µM or 0.01-2 µM etc. In other aspects, the compound of formula (I) inhibits the histone deacetylating activity of the HDAC isoform with a half maximal inhibitory concentration ($IC_{50}$) of 0.001-10 µM, or any number range in between, e.g., 0.001-8 µM, 0.002-8 µM, 0.002-6 µM, 0.003-6 µM, 0.003-4 µM, 0.005-4 µM, 0.005-2 µM or 0.01-2 µM etc. In yet other aspects, the compound of formula (I) inhibits the histone deacetylating activity of the HDAC isoform with a half maximal inhibitory concentration ($IC_{50}$) of 0.02-10 µM, or any number range in between, e.g., 0.05-10 µM, 0.05-9 µM, 0.1-9 µM, 0.1-8 µM, 0.2-8 µM, 0.2-7 µM, 0.4-7 µM or 0.4-6 µM etc. In further aspects, the compound of formula (I) inhibits the activity of the HDAC isoform with a half maximal inhibitory concentration ($IC_{50}$) of lower than 10 µM, lower than 8 µM, lower than 6 µM, lower than 4 µM, lower than 2 µM, lower than 1 µM, lower than 0.5 µM, lower than 0.2 µM, lower than 0.1 µM, etc.

In some embodiments, the compound inhibits the histone deacetylating activity of the HDAC isoform by at least 90%, at least 80%, at least 70%, at least 60%, at least 50%, at least 40%, at least 30%, at least 20%, or at least 10%. In other embodiments, the compound inhibits the histone deacetylating activity of the HDAC isoform by 10-100%, or any percent range in between, e.g., 10-90%, 15-90%, 30%-90%, 15-80%, 20-80%, 30%-80%, 20-70%, 25-70%, 30% -70%, 25-60%, 30-60%, or 30-50%, etc.

In some embodiments, the compound of formula (I) inhibits the histone deacetylating activity of the HDAC isoform, thereby inhibits cell proliferation, induces cell death, or both.

In some aspects, the method is performed in vitro. A non-limiting example is a screening assay using the compound of formula (I) as a positive control, a standard, or both to measure the activity of an unknown compound in inhibiting HDAC.

In some aspects, the method is performed in vivo, thereby inhibiting the HDAC isoform in a subject. The contacting is achieved by administering the compound, or a pharmaceutically acceptable salt form thereof, in an amount effective to inhibit the HDAC isoform. In other aspects, the subject is a human, e.g., a patient.

A cancer cell includes a cell derived from a tumor, neoplasm, cancer, precancer, cell line, or any other sources that is potentially capable of unlimited expansion and growth. In some aspects, the cancer cell is derived from a naturally occurring source. In other aspects, the cancer cell is artificially created. In some embodiments, the cancer cell is capable of invasion into a tissue and metastasis when placed into an animal host. Cancer cells further encompass any malignant cells that have invaded other tissues, metastasized, or both. In some aspects, one or more cancer cells of an organism is referred to as a cancer, a tumor, a neoplasm, a growth, a malignancy, or another term used in the art describing cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include: caspase dependent and independent pathways, autophagy, necrosis, apoptosis, and mitochondrial dependent and independent processes and further include any such processes yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g., macrophages and $CD8^+$ T cells) or endothelial cells that may differentiate into blood vessel structures in the process of angiogenesis or vasculogenesis.

Determination of an effective amount of the disclosed compound is within the capability of those skilled in the art, especially in light of the detailed disclosure provided herein. The effective amount of a pharmaceutical composition used to affect a particular purpose as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Methods of Treating a HDAC-Associated Disease

Herein the inventors also disclose a method of treating a histone deacetylase (HDAC)-associated disease, for example, a disease associated with a histone deacetylase (HDAC) isoform. Typically the method comprises administering to a subject any one of the disclosed compounds of formula (I), or a pharmaceutically acceptable salt form thereof.

Non-limiting examples of the disease include: a cell proliferative disease (e.g., cancer), an autoimmune disorder, an inflammatory disorder, a neurodegenerative disease, and combinations thereof, etc.

In some embodiments, the cell proliferative disease is cancer. Non-limiting examples of cancer include: acute lymphocytic leukemia (ALL), acute myeloid leukemia (AML), acute promyelocytic leukemia (APL), breast cancer, chronic myeloid leukemia (CML), colon cancer, diffuse large B-cell lymphoma (DLBCL), gastrointestinal stromal tumor (GIST), glioblastoma (GBM), hepatocellular carcinoma, Hodgkin's lymphoma, leukemia, lung cancer, multiple myeloma, non-Hodgkin's lymphoma, non-small cell lung cancer (NSCLC), neuroblastoma, ovarian cancer, pancreatic ductal adenocarcinoma, peripheral T-cell lymphoma, prostate cancer, uterine cancer, Waldenstrom myeloma, and combinations thereof, etc.

In some embodiments, the cancer is selected from the group consisting of: ovarian cancer, prostate cancer, lung cancer, acute myeloid leukemia, multiple myeloma, bladder carcinoma, renal carcinoma, breast carcinoma, colorectal carcinoma, neuroblastoma, melanoma, gastric cancer, and combinations thereof. In some aspects, the compound of formula (I) inhibits cancer cell proliferation, induces cancer cell death, or both.

Non-limiting examples of the autoimmune disorder or inflammatory disorder include: airway hyperresponsiveness, Crohn's disease, inflammatory bowel disease, multiple sclerosis, psoriasis, rheumatoid arthritis, systemic lupus erythematosus, type 1 diabetes, ulcerative colitis, and combinations thereof, etc.

Non-limiting examples of the neurodegenerative disorder include: Alzheimer's disease (AD), amyotrophic lateral sclerosis (ALS), cerebral ischemia, Huntington's disease (HD), Parkinson's disease (PD), spinal muscular atrophy, and combinations thereof, etc.

In some aspects, the disease is associated with HDAC1, HDAC2, HDAC3, HDAC4, HDAC5, HDAC6, HDAC7, HDAC8, HDAC9, HDAC10, HDAC11, or combinations thereof. In other aspects, the HDAC-associated disease is associated with HDAC1, HDAC3, HDAC6, HDAC10, or combinations thereof.

In certain more specific aspects of the invention, the compound of formula (I) inhibits the histone deacetylating activity of the HDAC isoform with a half maximal inhibitory concentration ($IC_{50}$) of 0.001-4 µM, or any number range in between, e.g., 0.001-3.5 µM, 0.002-3.5 µM, 0.002-3 µM, 0.003-3 µM, 0.003-2.5 µM, 0.005-2.5 µM, 0.005-2 µM or 0.01-2 µM etc.

In other aspects, the compound of formula (I) inhibits the histone deacetylating activity of the HDAC isoform with a half maximal inhibitory concentration ($IC_{50}$) of 0.001-10 µM, or any number range in between, e.g., 0.001-8 µM, 0.002-8 µM, 0.002-6 µM, 0.003-6 µM, 0.003-4 µM, 0.005-4 µM, 0.005-2 µM or 0.01-2 µM etc. In yet other aspects, the compound of formula (I) inhibits the histone deacetylating activity of the HDAC isoform with a half maximal inhibitory concentration ($IC_{50}$) of 0.02-10 µM, or any number range in between, e.g., 0.05-10 µM, 0.05-9 µM, 0.1-9 µM, 0.1-8 µM, 0.2-8 µM, 0.2-7 µM, 0.4-7 µM or 0.4-6 µM etc. In further aspects, the compound of formula (I) inhibits the activity of the HDAC isoform with a half maximal inhibitory concentration ($IC_{50}$) of lower than 10 µM, lower than 8 µM, lower than 6 µM, lower than 4 µM, lower than 2 µM, lower than 1 µM, lower than 0.5 µM, lower than 0.2 µM, lower than 0.1 µM, etc.

In some embodiments, the compound of formula (I) inhibits the histone deacetylating activity of the HDAC isoform by at least 90%, at least 80%, at least 70%, at least 60%, at least 50%, at least 40%, at least 30%, at least 20%, or at least 10%. In other embodiments, the compound inhibits the histone deacetylating activity of the HDAC isoform by 10-100%, or any percent range in between, e.g., 10-90%, 15-90%, 30%-90%, 15-80%, 20-80%, 30%-80%, 20-70%, 25-70%, 30%-70%, 25-60%, 30-60%, or 30-50%, etc.

In yet other aspects, the method further comprises administering a chemotherapy drug to the subject. In some embodiments, the chemotherapy drug comprises pomalidomide. In other embodiments, the chemotherapy drug comprises dexamethasone. In yet other embodiments, the chemotherapy drug comprises both pomalidomide and dexamethasone.

In some aspects, the composition is administered at 10-400 mg/kg, or any number in between, e.g., 10-350 mg/kg, 20-350 mg/kg, 20-300 mg/kg, 30-300 mg/kg, 30-250 mg/kg, 40-250 mg/kg, 40-200 mg/kg, 50-200 mg/kg, 50-150 mg/kg, 60-150 mg/kg, or 60-100 mg/kg, etc.

In other aspects, the composition is administered about every 4, 8, 12, 16, or 24 hours. In yet other aspects, the composition is administered every 1-24 hours, or any number in between, e.g., 2-24 hours, 2-18 hours, 3-18 hours, 3-16 hours, 4-16 hours, 4-12 hours, 5-12 hours, 5-8 hours, etc.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramucosal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery, topical application, local injection, or administration by a catheter, by a suppository, or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a pharmaceutical composition may be determined by standard pharmaceutical procedures in cell cultures or animals. Examples include the determination of the $IC_{50}$ (the half maximal inhibitory concentration) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of one of the disclosed compounds to result in the slowing of expansion of the cancer cells would preferably result in a concentration at or near the target tissue that is effective in slowing cellular expansion in neoplastic cells but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of one of the disclosed compounds encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include one of the disclosed compounds may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of one of the disclosed compounds to a diseased entity. An example of such a kit includes one or more unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including one of the disclosed compounds may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology,* 2d Ed., W. B. Saunders Co., Philadelphia, pp. 68-79). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype). Further examples include leukoplakia (a benign-appearing hyperplastic or dysplastic lesion of the epithelium) or Bowen's disease (a carcinoma in situ), which are pre-neoplastic lesions indicating the desirability of prophylactic intervention. In another example, fibrocystic disease, including cystic hyperplasia, mammary dysplasia, adenosis, or benign epithelial hyperplasia, indicates the desirability of prophylactic intervention.

In some aspects of the invention, use of the disclosed compound may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, *Arch. Pathol. Lab. Med.* 124:966-78, 2000. Tumors that are hormone receptor positive are more likely to respond to hormone therapy and also typically grow less aggressively, thereby resulting in a better prognosis for patients with $ER^+/PR^+$ tumors. In a further example, overexpression of human epidermal growth factor receptor 2 (HER-2/neu), a transmembrane tyrosine kinase receptor protein, has been correlated with poor breast cancer prognosis (see, e.g., Ross et al, *The Oncologist* 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t(14;18) for follicular lymphoma; an incidence of polyposis or Gardner's syndrome that are indicative of colon cancer; benign monoclonal gammopathy which is indicative of multiple myeloma; kinship with persons who have had or currently have a cancer or precancerous disease; exposure to carcinogens; or any other predisposing factor that indicates in increased incidence of cancer now known or yet to be disclosed.

The invention further encompasses methods of treating cancer that comprise combination therapies, wherein the combination therapies comprise the administration of a pharmaceutical composition including one of the disclosed compounds and another treatment modality. Such treatment modalities include, but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modalities may be used effectively. This in turn reduces the toxicity and side effects, if any, associated with the administration either modality without a reduction in efficacy.

In another aspect of the invention, the pharmaceutical composition including one of the disclosed compounds is administered in combination with a therapeutically effective amount of radiotherapy. Radiotherapy may be administered concurrently with, prior to, or following the administration of the pharmaceutical composition including the compound. Radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination with one of the disclosed compounds include nucleic acid binding compositions, such as cis-diamminedichloro platinum (II) (cisplatin), doxorubicin, 5-fluorouracil, taxol, and topoisomerase inhibitors such as etoposide, teniposide, irinotecan, and topotecan. Still other pharmaceutical compositions include antiemetic compositions, such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron.

Still other examples of pharmaceutical compositions that may be used in combination with the pharmaceutical composition including one of the disclosed compounds are hematopoietic colony stimulating factors. Examples of hematopoietic colony stimulating factors include, but are not limited to, filgrastim, sargramostim, molgramostim, and epoietin alfa. Alternatively, the pharmaceutical composition including one of the disclosed compounds may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include one of the disclosed compounds may include analgesic agents. Such agents may be opioid or non-opioid analgesic. Non-limiting examples of opioid analgesics include morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac, or any other analgesic now known or yet to be disclosed.

In other aspects of the invention, pharmaceutical compositions including one of the disclosed compounds may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including one of the disclosed compounds may then be administered to the patient prior to restoring the entity's bone marrow by addition of either the patient's own or donor stem cells.

Cancers that may be treated by pharmaceutical compositions including the one of the disclosed compounds either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Examples that represent different aspects of the invention follow. Such examples should not be construed as limiting the scope of the disclosure. Alternative mechanistic pathways and analogous structures within the scope of the invention would be apparent to those skilled in the art.

EXAMPLES

Elements and acts in the example are intended to illustrate the invention for the sake of simplicity and have not necessarily been rendered according to any particular sequence or embodiment. The example is also intended to establish possession of the invention by the Inventors.

Example 1. Example Compounds of Formula (I) or Formula (II)

4-((1-(cyclohexylmethyl)-1H-benzo[d]imidazol-2-yl)amino)-N-hydroxybenzamide (ID #1)

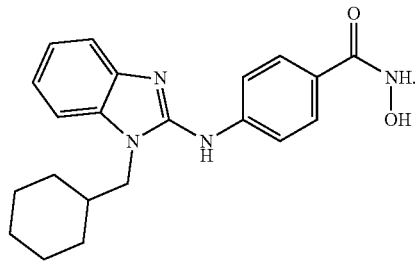 [SMILES: O=C(NO)c1ccc(Nc2nc3ccccc3n2CC2CCCCC2)cc1]

4-((1-cyclohexyl-1H-benzo[d]imidazol-2-yl)amino)-N-hydroxybenzamide (ID #2)

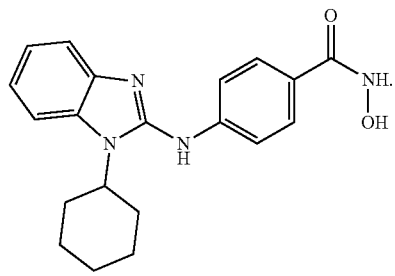 [SMILES: O=C(NO)c1ccc(Nc2nc3ccccc3n2C2CCCCC2)cc1]

4-((1-cycloheptyl-1H-benzo[d]imidazol-2-yl)amino)-N-hydroxybenzamide (ID #3)

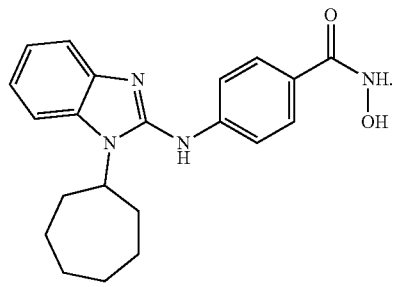 [SMILES: O=C(NO)c1ccc(Nc2nc3ccccc3n2C2CCCCCC2)cc1]

31

4-((1-(1-fluorocyclohexyl)methyl)-1H-benzo[d]imidazol-2-yl)amino)-N-hydroxybenzamide (ID #4)

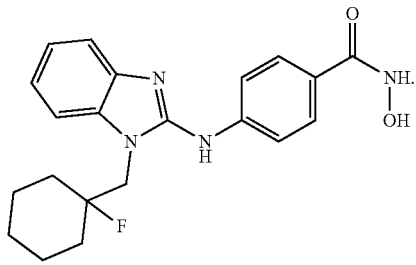 [SMILES: O=C(NO)c1ccc(Nc2nc3ccccc3n2CC2(F)CCCCC2)cc1]

4-((1-(cyclopentylmethyl)-1H-benzo[d]imidazol-2-yl)amino)-N-hydroxybenzamide (ID #5)

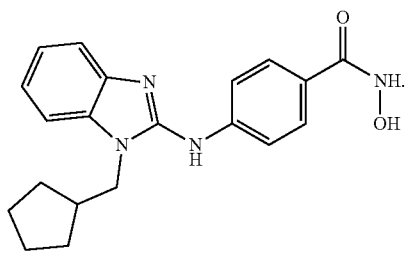 [SMILES: O=C(NO)c1ccc(Nc2nc3ccccc3n2CC2CCCC2)cc1]

4-((1-(2-cyclopentylethyl)-1H-benzo[d]imidazol-2-yl)amino)-N-hydroxybenzamide

ID #6

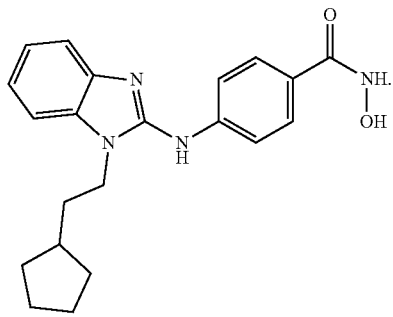 [SMILES: O=C(NO)c1ccc(Nc2nc3ccccc3n2CCC2CCCC2)cc1]

32

4-((1-(4,4-difluorocyclohexyl)methyl)-1H-benzo[d]imidazol-2-yl)amino)-N-hydroxybenzamide (ID #7)

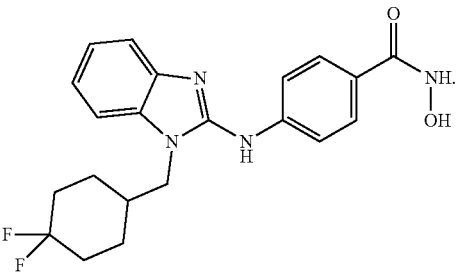 [SMILES: O=C(NO)c1ccc(Nc2nc3ccccc3n2CC2CCC(F)(F)CC2)cc1]

4-((1-(4,4-difluorocyclohexyl)methyl)-5-fluoro-1H-benzo[d]imidazol-2-yl)amino)-N-hydroxybenzamide (ID #8)

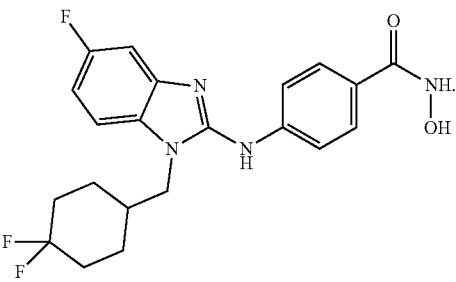 [SMILES: O=C(NO)c1ccc(Nc2nc3cc(F)ccc3n2CC2CCC(F)(F)CC2)cc1]

N-hydroxy-4-((1-((tetrahydro-2H-pyran-4-yl)methyl)-1H-benzo[d]imidazol-2-yl)amino)benzamide (ID #9)

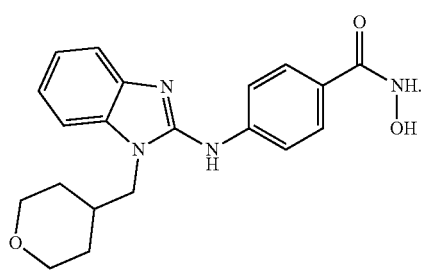 [SMILES: O=C(NO)c1ccc(Nc2nc3ccccc3n2CC2CCOCC2)cc1]

4-((5-fluoro-1-((tetrahydro-2H-pyran-4-yl)methyl)-1H-benzo[d]imidazol-2-yl)amino)-N-hydroxybenzamide (ID #10)

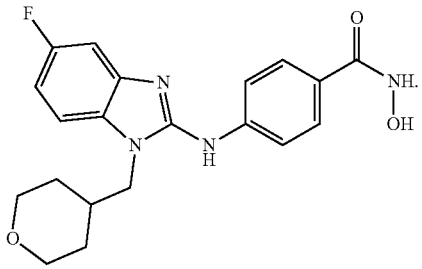 [SMILES: O=C(NO)c1ccc(Nc2nc3cc(F)ccc3n2CC2CCOCC2)cc1]

Example 2. Cell Viability Assays with MM1.S Cells

Cell viability in the presence of varying concentrations of the above listed compounds at different time points was used to assess cytotoxicity and the effect of the compounds on cell proliferation. $IC_{50}$ (or percent activity) data for the disclosed compounds in the MM1.S cell line are summarized in Table 2.

Cell Viability Assay—Cell viability was measured by the CellTiter-GlO® cell viability assay from Promega (Madison, Wis.). The CellTiter-GlO® Luminescent Cell Viability Assay is a homogeneous method to determine the number of viable cells in culture based on quantitation of the ATP present, which signals the presence of metabolically active cells. Following treatment, CellTiter-GlO® is added to treatment wells and incubated at 37° C. luminescence values were measured at using a Molecular Devices Spectramax microplate reader Single Agent Studies—Cells were grown to 70% confluency, trypsinized, counted, and seeded in 96 well flat-bottom plates at a final concentration of $2.5\times10^3$-$5\times10^3$ cells/well (Day 0). Cells were allowed to incubate in growth media for 24 hours. Treatment with the test agents or standard agents began on Day 1 and continued for 72 hours. At the 72 hour timepoint, treatment containing media was removed. Viable cell numbers are quantified by the CellTiter-GlO® cell viability assay as described above. Results from these studies were used to calculate an $IC_{50}$ value (concentration of drug that inhibits cell growth by 50 percent of control) for each compound.

Data Collection—For single agent and combination studies, data from each experiment was collected and expressed as % Cell Growth using the following calculation:

Cell Growth=$(f_{test}/f_{vehicle})\times100$

Where $f_{test}$ is the fluorescence of the tested sample, and $f_{vehicle}$ is the fluorescence of the vehicle in which the drug is dissolved. Dose response graphs and $IC_{50}$ values were generated using Prism 6 software (GraphPad) using the following equation:

$$Y = \frac{(\text{Top-Bottom})}{(1 + 10^{((\log IC50-X)-HillSlope)})}$$

Where X is the logarithm of concentration and Y is the response. Y starts at the Bottom and goes to Top with a sigmoid shape.

TABLE 2

| $IC_{50}$ of example compounds in MM1.S cells ||
| Compound ID # | $IC_{50}$ in MM1.S (μM) |
| --- | --- |
| 1 | 0.5 |
| 2 | 2.0 |
| 3 | 2.1 |
| 4 | 2.6 |
| 5 | 2.2 |
| 6 | 1.1 |
| 7 | 0.7 |
| 8 | 1.2 |
| 9 | 2.9 |
| 10 | 2.9 |

Example 3. Cell Viability Assays with Various Cell Lines

Compound ID #1 (a compound of formula (I)) and Compound ID #3 (a compound of formula (II)) were tested for the inhibition of cancer cell proliferation. Cell viability in the presence of varying concentrations of Compound ID #1 and Compound ID #3 at different time points was used to assess cytotoxicity and the effect of the compounds on cell proliferation. The 50% inhibitory concentration (IC50) data for the compounds is summarized in Table 3. The data clearly show the surprising and unexpected increased anti-cancer activity associated with Compound ID #1 compared to Compound ID #3.

Cell Viability Assay—Cell viability was measured by the CellTiter-Glo® cell viability assay Promega (Madison, Wis.). The CellTiter-Glo® Luminescent Cell Viability Assay is a homogeneous method to determine the number of viable cells in culture based on quantitation of the ATP present, which signals the presence of metabolically active cells. Following treatment, CellTiter-Glo® is added to treatment wells and incubated at 37° C. luminescence values were measured at using a Molecular Devices Spectramax microplate reader.

Single Agent Studies—Cells were grown to 70% confluency, trypsinized, counted, and seeded in 96 well flat-bottom plates at a final concentration of $2.5\times10^3$-$5\times10^3$ cells/well (Day 0). Cells were allowed to incubate in growth media for 24 hours. Treatment with the test agents began on Day 1 and continued for 72 hours. At the 72-hour time point, treatment-containing media was removed. Viable cell numbers are quantified by the CellTiter-Glo® cell viability assay as described above. Experiments were run with triplicate concentrations to determine growth inhibitory activity. Results from these studies were used to calculate an $IC_{50}$ value (concentration of drug that inhibits cell growth by 50 percent of control) for each compound.

Data Collection—For single agent and combination studies, data from each experiment was collected and expressed as % Cell Growth using the following calculation:

% Cell Growth=$(f_{test}/f_{vehicle})\times100$

Where $f_{test}$ is the luminescence of the tested sample, and $f_{vehicle}$ is the luminescence of the vehicle in which the drug is dissolved. Dose response graphs and $IC_{50}$ values were generated using Prism 6 software (GraphPad).

TABLE 3

| Tumor Type | Cell line | ID #1 IC$_{50}$ (µM) | ID #3 IC$_{50}$ (µM) | Improvement ID #1 over ID #3 | |
|---|---|---|---|---|---|
| | | | | fold | Percent |
| GBM | U251 | 1.58 | 4.07 | 2.58 | 61.18% |
| Breast | MDA-157 | 2.75 | 7.59 | 2.76 | 63.77% |
| Breast | MDA468 | 3.86 | 9.33 | 2.42 | 58.63% |
| Breast | MCF7 | 1.96 | 3.55 | 1.81 | 44.79% |
| GIST | GIST48 | 1.32 | 4.24 | 3.21 | 68.87% |
| GIST | GIST882 | 5.75 | 17.78 | 3.09 | 67.66% |
| Uterine | AN3CA | 1.60 | 4.57 | 2.86 | 64.99% |
| Uterine | MFE280 | 5.01 | 9.71 | 1.94 | 48.40% |
| Uterine | SKUT-1 | 3.80 | 9.55 | 2.51 | 60.21% |
| Uterine | SKUT-1B | 2.51 | 6.92 | 2.76 | 63.73% |
| Uterine | MFE296 | 4.37 | 12.59 | 2.88 | 65.29% |
| Uterine | Ishikawa | 1.70 | 4.37 | 2.57 | 61.10% |
| Uterine | SNG-M | 1.70 | 8.07 | 4.75 | 78.93% |
| Myeloma | H929 | 0.83 | 1.38 | 1.66 | 39.86% |
| Myeloma | MM1.S | 0.50 | 2.09 | 4.18 | 76.08% |
| Myeloma | KMS-11 | 1.42 | 3.02 | 2.13 | 52.98% |
| Myeloma | KMS-34 | 0.61 | 1.36 | 2.23 | 55.15% |
| Myeloma | RPMI-8226 | 0.66 | 1.51 | 2.29 | 56.29% |
| Myeloma | U266 | 1.17 | 4.1 | 3.50 | 71.46% |
| ALL | RS4-11 | 1.10 | 2.44 | 2.22 | 54.92% |
| AML | MV411 | 0.63 | 2.75 | 4.37 | 77.09% |
| CML | K562 | 1.58 | 5.25 | 3.32 | 69.90% |
| Lymphoma | SUDHL-4 | 0.24 | 4.17 | 17.38 | 94.24% |
| Lymphoma | SUDHL-10 | 0.55 | 1.51 | 2.75 | 63.58% |
| Lymphoma | OCI-LY3 | 1.05 | 2.29 | 2.18 | 54.15% |
| Lymphoma | RAMOS | 1.38 | 2.88 | 2.09 | 52.08% |
| Lymphoma | Raji | 1.83 | 4.83 | 2.64 | 62.11% |
| Lymphoma | Mino | 1.20 | 4.17 | 3.48 | 71.22% |
| Lymphoma | BC-1 | 1.79 | 4.93 | 2.75 | 63.69% |
| Lymphoma | JEKO | 0.97 | 2.22 | 2.29 | 56.31% |
| Lymphoma | Toledo | 0.81 | 3.21 | 3.96 | 74.77% |
| NSCLC | A549 | 2.29 | 10 | 4.37 | 77.10% |
| NSCLC | H1650 | 6.61 | 18.2 | 2.75 | 63.68% |
| NSCLC | H460 | 3.47 | 10.47 | 3.02 | 66.86% |
| NSCLC | H1437 | 2.19 | 4.79 | 2.19 | 54.28% |
| Ovarian | ES2 | 3.98 | 13.18 | 3.31 | 69.80% |
| Ovarian | A2780 | 2.03 | 5.58 | 2.75 | 63.62% |

Example 4. In Vivo Screening in a Model of Human Myeloma

Single Agent Screening

In vivo efficacy studies of Compound ID #1, Compound ID #2, and Compound ID #3 were tested in human MM1.S xenograft model as shown in FIG. 1. Female athymic nude mice were inoculated with 5.0×10$^6$ MM1.S human myeloma cells suspended in a mixture of 50% Matrigel and 50% tissue culture media in a total volume of 100 µL. Eighteen days following inoculation, the mice were pair-matched into four groups of five mice per group at an average tumor volume of 171 mm$^3$ per group. Group 1 (G1) was treated with vehicle only daily for 19 days. Group 2 (G2) was treated with Compound ID #1 at 100 mg/kg daily for 19 days. Group 3 (G3) was treated with Compound ID #2 at 100 mg/kg daily for 19 days. Group 4 (G4) was treated with Compound ID #3 at 100 mg/kg daily for 19 days. Vehicle and Compound ID #1, Compound ID #2 and Compound ID #3 were administered orally via oral gavage. Body weights and tumor measurements were collected twice weekly. Tumor width and length were measured in millimeters and converted to tumor volume (in cubic millimeters) using the formula:

$$\text{tumor volume (mm}^3) = \frac{\text{width}^2 \times \text{length}}{2}.$$

Compound ID #1 demonstrated significantly superior anticancer activity when compared to either Compound ID #2 or Compound ID #3 (FIG. 1).

2. Combination Screening

Figure 2:
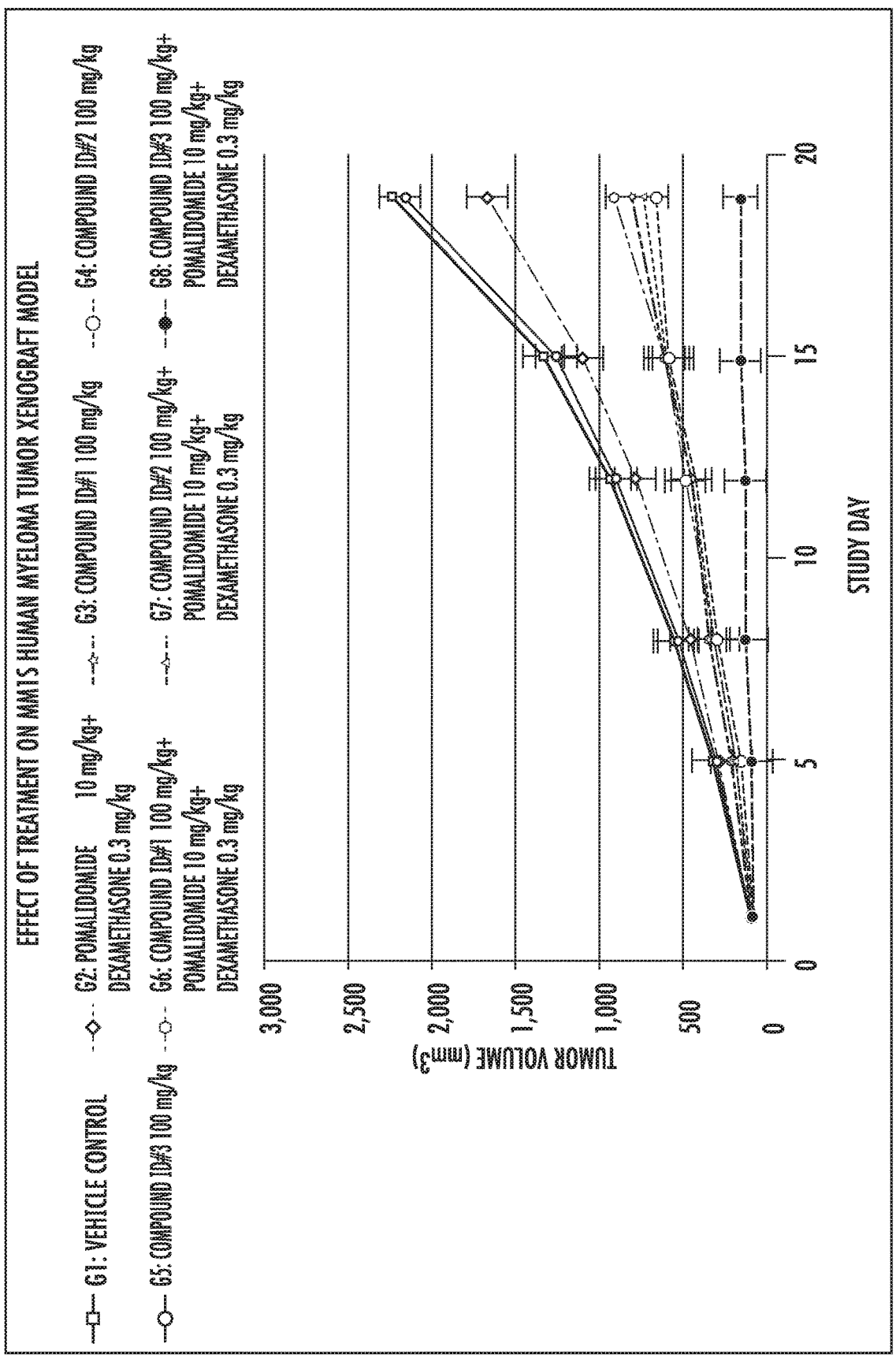
FIG. 2 depicts the effect of treatment with Compound ID #1, Compound ID #2, or Compound ID #3 in combination with dexamethasone and pomalidomide on tumor volume in a human myeloma tumor xenograft model.

Compound ID #1, Compound ID #2 and Compound ID #3 were tested in combination with the FDA approved anticancer drug Pomalyst (pomalidomide) (FIG. 2). Female athymic nude mice were inoculated with 5.0×10$^6$ MM1.S human myeloma cells suspended in a mixture of 50% Matrigel and 50% tissue culture media in a total volume of 100 µL. Eighteen days following inoculation, the mice were pair-matched into four groups of five mice per group at an average tumor weight of 171 mm$^3$ per group. Group 1 (G1) was treated with vehicle only daily for 19 days. Group 2 (G2) was treated orally with pomalidomide at 10 mg/kg and intraperitoneally with dexamethasone at 0.3 mg/kg daily for 4 days per week for to Day 19. Group 3 (G3) was treated with Compound ID #1 at 100 mg/kg daily for 19 days. Group 4 (G4) was treated with Compound ID #2 at 100 mg/kg daily for 19 days. Group 5 (G5) was treated with Compound ID #3 at 100 mg/kg daily for 19 days. Group 6 (G6) was treated with Compound ID #1 at 100 mg/kg daily for 19 days plus pomalidomide/dexamethasone. Group 7 (G7) was treated with Compound ID #2 at 100 mg/kg daily for 19 days plus pomalidomide/dexamethasone. Group 8 (G8) was treated with Compound ID #3 at 100 mg/kg daily for 19 days plus pomalidomide/dexamethasone. Vehicle and Compound ID #1, Compound ID #2 and Compound ID #3 were administered orally via oral gavage. Body weights and tumor measurements were collected twice weekly. Tumor width and length were measured in millimeters and converted to tumor volume (in cubic millimeters) using the formula:

$$\text{tumor volume (mm}^3) = \frac{\text{width}^2 \times \text{length}}{2}.$$

Compound ID #1 demonstrated significantly superior anticancer activity when combined with pomalidomide/dexamethasone compared to either Compound ID #2 or ID #3 when combined with pomalidomide/dexamethasone (FIG. 2).

Example 5. In Vitro HDAC Enzyme Inhibition

Purified histone deacetylase enzymes 1, 3, 6, 10 were incubated with fluorescently labeled substrate and test compounds in a standardized reaction mixture in 384 well plates. Upon termination of the reaction, samples were introduced onto microfluidic chips. Samples migrate through channels in the chips and product and substrate are separated based on the difference in their charge and mass (electrophoretic mobility shift). Enzyme activity is measured by direct comparison of the fluorescence in the product and substrate peaks and the results presented in Table 4.

TABLE 4

| Compound | HDAC1 (IC$_{50}$ µM) | HDAC3 (IC$_{50}$ µM) | HDAC6 (IC$_{50}$ µM) | HDAC10 (IC$_{50}$ µM) |
|---|---|---|---|---|
| ID #1 | 0.130 | 0.019 | 0.0064 | 0.137 |
| ID #2 | 0.385 | 0.068 | 0.015 | 3.56 |
| ID #3 | 0.445 | 0.079 | 0.0145 | 3.12 |

Compound ID #1 demonstrated more potent inhibition of the HDAC isoforms tested.

Example 6. Pharmacokinetic Studies

Plasma samples were collected from healthy mice and analyzed for levels of compound ID #1, ID #2, and ID #3 and reported in Table 5. In brief, compounds were individually and accurately weighed out to produce a stock solution in Dimethyl-sulfoxide (DMSO) at a concentration of 2 mg/mL and stored at −20° C. From the stock solution, a working stock was prepared by diluting it in Methanol-Water 50:50 (v/v) at 20 μg/mL for calibration curve preparation and stored at 4° C. Standards used for quantitation and quality control samples (QC's) were prepared on the same day of sample processing using blank plasma obtained from non-treated mice. For each analyte, standards were prepared through serial dilution of the working stock at concentrations of 0.1, 0.5, 1.0, 10, 50, 100, 500 and 1000 ng/mL; QC's were prepared at intermediate concentrations of 0.75, 7.5, 75 and 750 ng/mL. Plasma samples were stored at −80° C. until ready for analysis and then placed on ice for thawing. An aliquot of 20 μL for samples, standards and QC's, were transferred into a 96-well extraction plate according to a pre-defined layout. Appropriate volume of Methanol-Formic Acid 99.9-0.1 containing internal standard (Verapamil at 25 ng/mL) was added to each well and samples were extracted under vacuum. Eluent was then transferred into a LCMS plate for analysis using a suitable column for separation and MRM detection. Concentration of analytes was calculated based on the calibration curve and analyzed for pharmacokinetic parameters by using Non-compartmental analysis (NCA) using WinNonlin Phoenix software. Parameters such as Cmax, Tmax, half-life, AUC(0-last), AUC(0-∞), volume of distribution (Vss) and clearance (Cl/F) were reported.

The analogs were tested for pharmacokinetic analysis in the mouse with doses of 1 mg/kg for intravenous (IV) route and 5 mg/kg for oral (P0) route. The IV dose showed that out of the three analogs, compound ID #1 showed a longer half-life than did the other 2 analogs (3.7 hr versus 1.2 and 2.37 hr, respectively). Overall exposure following IV dose also favored compound ID #1 with AUC0-∞ 1488.1 hr*ng/mL whereas compound ID #2 and ID #3 were 329.1 and 1193.7 hr*ng/mL, respectively.

Similarly, following oral dose all three compounds showed rapid absorption (<1 hr) with compound ID #1 showing the highest maximal concentration at 757.4 ng/mL, whereas compounds ID #2 and ID #3 achieved 407.1 and 348.6 ng/mL, respectively. Overall exposure following oral doses also clearly distinguished compound ID #1 with AUC0-∞ at 3974.8 ng/mL*hr, while compounds ID #2 and ID #3 showed 1277.3 and 1648.6 ng/mL*hr, respectively.

TABLE 5

| PK parameters | ID#1 1.0 mg/kg IV | ID#1 5.0 mg/kg PO | ID#2 1.0 mg/kg IV | ID#2 5.0 mg/kg PO | ID#3 1.0 mg/kg IV | ID#3 5.0 mg/kg PO |
|---|---|---|---|---|---|---|
| Rsq (>0.85) | 0.97 | 0.99 | 0.85 | 1.00 | 0.92 | 1.00 |
| Half-life (hr) | 3.70 | 3.39 | 1.20 | 2.56 | 2.37 | 2.99 |
| Tmax (hr) | 0.08 | 0.50 | 0.08 | 0.50 | 0.08 | 0.25 |
| Cmax (ng/mL) | 1288.53 | 757.43 | 508.17 | 407.10 | 829.80 | 348.57 |
| AUC$_{0\text{-}last}$ (hr*ng/mL) | 1444.47 | 3222.99 | 324.40 | 1275.41 | 1191.74 | 1642.27 |
| AUC$_{0\text{-}\infty}$ (hr*ng/mL) | 1488.05 | 3974.82 | 329.14 | 1277.26 | 1193.68 | 1648.60 |
| AUC % Extrap | 0.25 | 0.75 | 1.44 | 0.14 | 0.16 | 0.38 |
| Vss (L/kg) | 1.21 | — | 3.50 | — | 1.96 | — |
| Vz/F obs (L/kg) | — | 6.16 | — | 14.48 | — | 13.09 |
| Cl/F obs (L/hr/kg) | 0.69 | 1.26 | 3.04 | 3.91 | 0.84 | 3.03 |
| % F | — | 53.42 | — | 77.61 | — | 27.62 |
| Permeabiltiy (PAMPA) | 16.75 nm/s | | 16.51 nm/s | | 22.01 nm/s | |
| % PPB (m, r, hu) | 99.55; 99.83; 99.44 | | N/A | | 99.48; 99.45; 99.36 | |
| S9 in vitro half-life | 74.82 min | | >90 min | | 72.91 | |

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method of inhibiting the histone deacetylating activity of a histone deacetylase (HDAC) isoform in a cell, comprising contacting the cell with a compound of formula (I):

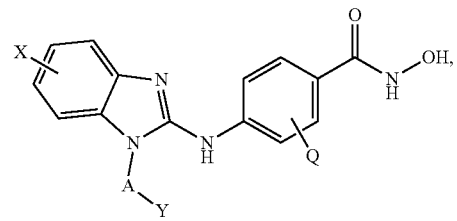

wherein:
X is selected from the group consisting of: H, halo, —C$_1$-C$_6$ alkyl, aryl, —C$_3$-C$_7$ cycloalkyl, and -3- to 10-membered heterocycle, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl;

A is selected from the group consisting of: a bond, —C$_1$-C$_6$ alkyl, and —C$_3$-C$_7$ cycloalkyl, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl;

Y is selected from the group consisting of: H, —C$_1$-C$_6$ alkyl, —C$_3$-C$_7$ cycloalkyl, aryl, and -3- to 10-membered heterocycle, any of which is unsubstituted, or substituted with one or more of: -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl; and Q is selected from the group consisting of: —H, -halo, —C$_1$-C$_6$ alkyl, —O—(C$_1$-C$_6$ alkyl), —OH, —CN, —COOR', —OC(O)R', NHR', N(R')$_2$, —NHC(O)R', and —C(O)NHR', wherein R' is —H or —C$_1$-C$_6$ alkyl;

wherein the compound inhibits the histone deacetylating activity of the HDAC isoform in the cell.

2. The method of claim 1, wherein X is H or halo; Q is H; and A is a bond or —C$_1$-C$_6$ alkyl.

3. The method of claim 2, wherein Y is —C$_3$-C$_7$ cycloalkyl, unsubstituted, or substituted with one or more of: -halo and -3- to 10-membered heterocycle.

4. The method of claim 1, wherein the compound is selected from the group consisting of:

4-((1-(cyclohexylmethyl)-1H-benzo[d]imidazol-2-yl)amino)-N-hydroxybenzamide (ID #1)

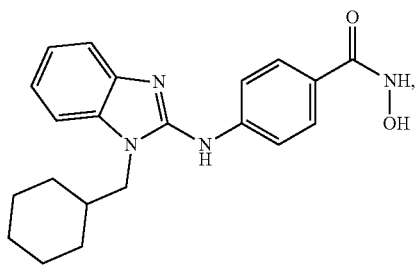 [SMILES: O=C(NO)c1ccc(Nc2nc3ccccc3n2CC2CCCCC2)cc1]

4-((1-cyclohexyl-1H-benzo[d]imidazol-2-yl)amino)-N-hydroxybenzamide (ID #2)

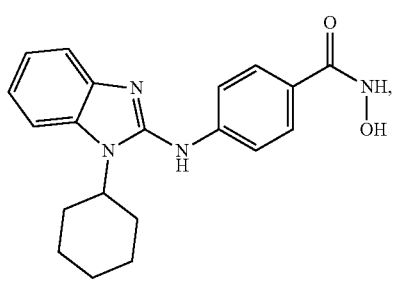 [SMILES: O=C(NO)c1ccc(Nc2nc3ccccc3n2C2CCCCC2)cc1]

4-((1-cycloheptyl-1H-benzo[d]imidazol-2-yl)amino)-N-hydroxybenzamide (ID #3)

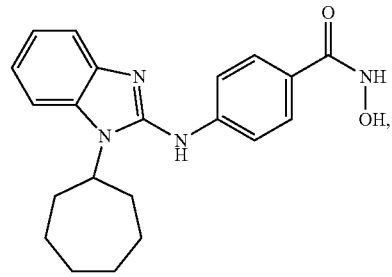 [SMILES: O=C(NO)c1ccc(Nc2nc3ccccc3n2C2CCCCCC2)cc1]

4-((1-((1-fluorocyclohexyl)methyl)-1H-benzo[d]imidazol-2-yl)amino)-N-hydroxybenzamide (ID #4)

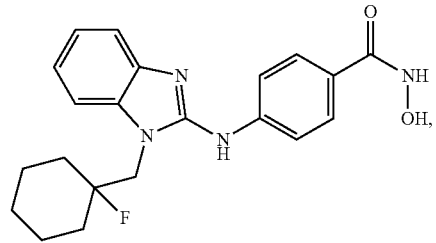 [SMILES: O=C(NO)c1ccc(Nc2nc3ccccc3n2CC2(F)CCCCC2)cc1]

4-((1-(cyclopentylmethyl)-1H-benzo[d]imidazol-2-yl)amino)-N-hydroxybenzamide (ID #5)

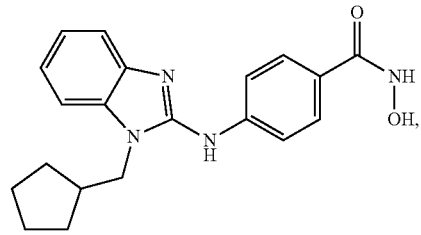 [SMILES: O=C(NO)c1ccc(Nc2nc3ccccc3n2CC2CCCC2)cc1]

4-((1-(2-cyclopentylethyl)-1H-benzo[d]imidazol-2-yl)amino)-N-hydroxybenzamide (ID #6)

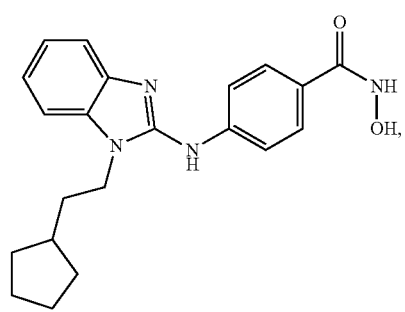 [SMILES: O=C(NO)c1ccc(Nc2nc3ccccc3n2CCC2CCCC2)cc1]

4-((1-((4,4-difluorocyclohexyl)methyl)-1H-benzo[d]imidazol-2-yl)amino)-N-hydroxybenzamide (ID #7)

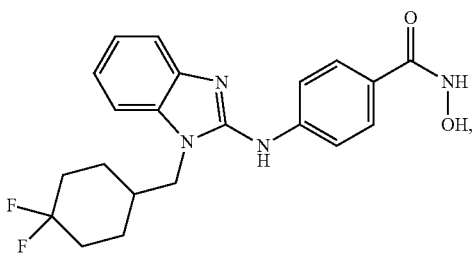 [SMILES: O=C(NO)c1ccc(Nc2nc3ccccc3n2CC2CCC(F)(F)CC2)cc1]

4-((1-((4,4-difluorocyclohexyl)methyl)-5-fluoro-1H-benzo[d]imidazol-2-yl)amino)-N-hydroxybenzamide (ID #8)

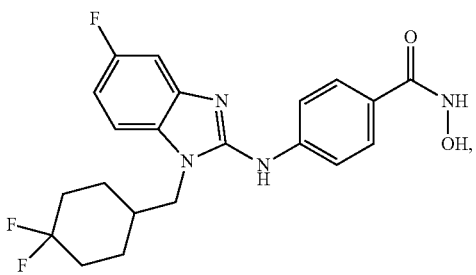 [SMILES: O=C(NO)c1ccc(Nc2nc3cc(F)ccc3n2CC2CCC(F)(F)CC2)cc1]

N-hydroxy-4-((1-((tetrahydro-2H-pyran-4-yl)methyl)-1H-benzo[d]imidazol-2-yl)amino)benzamide (ID #9)

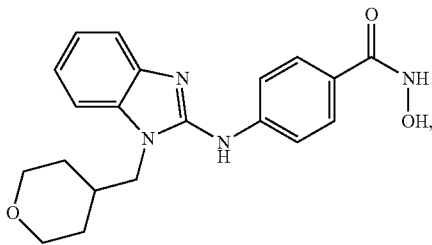 [SMILES: O=C(NO)c1ccc(Nc2nc3ccccc3n2CC2CCOCC2)cc1]

and 4-((5-fluoro-1-((tetrahydro-2H-pyran-4-yl)methyl)-1H-benzo[d]imidazol-2-yl)amino)-N-hydroxybenzamide (ID #10)

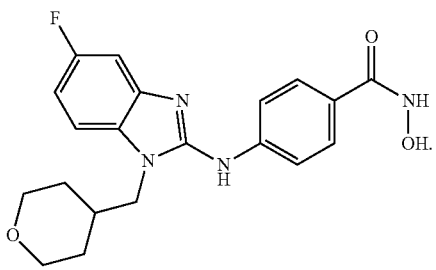 [SMILES: O=C(NO)c1ccc(Nc2nc3cc(F)ccc3n2CC2CCOCC2)cc1]

5. The method of claim 1, further comprising determining an expression signature in the cell that indicates the likely response to treatment with the compound, wherein the expression signature comprises expression of the HDAC isoform.

6. The method of claim 5, wherein the HDAC isoform is selected from the group consisting of: HDAC1, HDAC3, HDAC6, and HDAC10.

7. The method of claim 1, wherein the cell is selected from the group consisting of: a cancer cell, a neuronal cell, a cell of the immune system, a cell of the circulatory system, and combinations thereof.

8. A method of treating a subject having a disease by inhibiting an HDAC isoform, comprising administering to the subject a compound of formula (I):

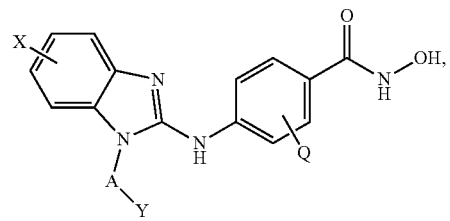

wherein:

X is selected from the group consisting of: H, halo, —$C_1$-$C_6$ alkyl, aryl, —$C_3$-$C_7$ cycloalkyl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl;

A is selected from the group consisting of: a bond, —$C_1$-$C_6$ alkyl, and —$C_3$-$C_7$ cycloalkyl, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl;

Y is selected from the group consisting of: H, —$C_1$-$C_6$ alkyl, —$C_3$-$C_7$ cycloalkyl, aryl, and -3- to 10-membered heterocycle, any of which is unsubstituted, or substituted with one or more of: -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl; and Q is selected from the group consisting of: —H, -halo, —$C_1$-$C_6$ alkyl, —O—($C_1$-$C_6$ alkyl), —OH, —CN, —COOR', —OC(O)R', NHR', N(R')$_2$, —NHC(O)R', and —C(O)NHR', wherein R' is —H or —$C_1$-$C_6$ alkyl;

wherein the compound inhibits the histone deacetylating activity of the HDAC isoform and the disease is a cancer selected from the group consisting of acute lymphocytic leukemia (ALL), acute myeloid leukemia (AML), acute promyelocytic leukemia (APL), breast cancer, chronic myeloid leukemia (CML), gastrointestinal stromal tumor (GIST), glioblastoma (GBM), lymphoma, myeloma, ovarian cancer, uterine cancer, and non-small cell lung cancer (NSCLC).

9. The method of claim 8, wherein X is H or halo; Q is H; and A is a bond or —$C_1$-$C_6$ alkyl.

10. The method of claim 9, wherein Y is —$C_3$-$C_7$ cycloalkyl, unsubstituted, or substituted with one or more of: -halo and -3- to 10-membered heterocycle.

11. The method of claim 8, wherein the compound is selected from the group consisting of:

4-((1-(cyclohexylmethyl)-1H-benzo[d]imidazol-2-yl)amino)-N-hydroxybenzamide (ID #1)

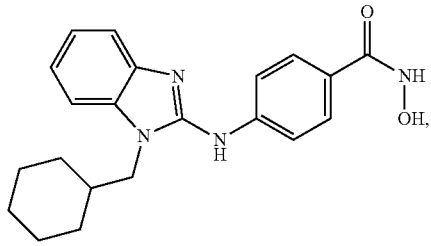 [SMILES: O=C(NO)c1ccc(Nc2nc3ccccc3n2CC2CCCCC2)cc1]

4-((1-cyclohexyl-1H-benzo[d]imidazol-2-yl)amino)-N-hydroxybenzamide (ID #2)

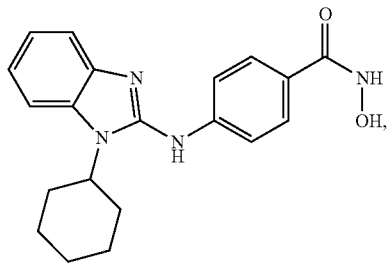 [SMILES: O=C(NO)c1ccc(Nc2nc3ccccc3n2C2CCCCC2)cc1]

4-((1-cycloheptyl-1H-benzo[d]imidazol-2-yl)amino)-N-hydroxybenzamide (ID #3)

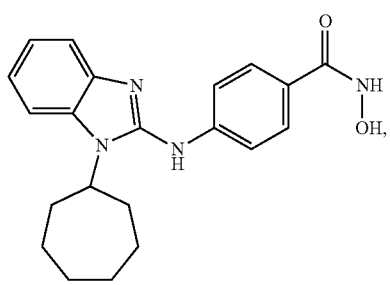 [SMILES: O=C(NO)c1ccc(Nc2nc3ccccc3n2C2CCCCCC2)cc1]

4-((1-((1-fluorocyclohexyl)methyl)-1H-benzo[d]imidazol-2-yl)amino)-N-hydroxybenzamide (ID #4)

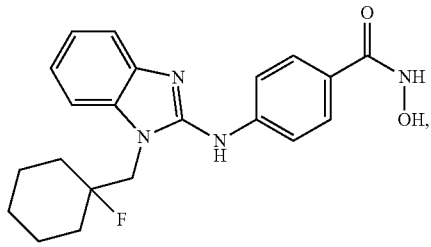 [SMILES: O=C(NO)c1ccc(Nc2nc3ccccc3n2CC2(F)CCCCC2)cc1]

4-((1-(cyclopentylmethyl)-1H-benzo[d]imidazol-2-yl)amino)-N-hydroxybenzamide (ID #5)

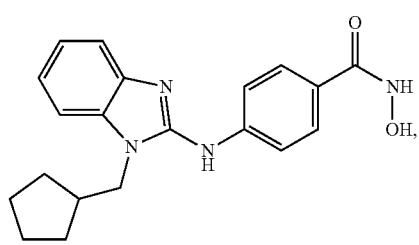 [SMILES: O=C(NO)c1ccc(Nc2nc3ccccc3n2CC2CCCC2)cc1]

4-((1-(2-cyclopentylethyl)-1H-benzo[d]imidazol-2-yl)amino)-N-hydroxybenzamide (ID #6)

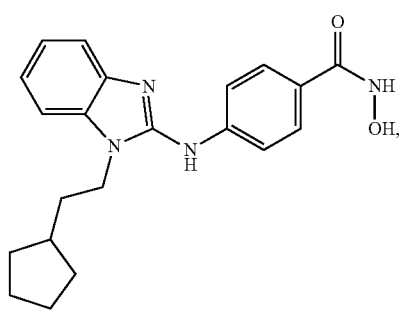 [SMILES: O=C(NO)c1ccc(Nc2nc3ccccc3n2CCC2CCCC2)cc1]

4-((1-((4,4-difluorocyclohexyl)methyl)-1H-benzo[d]imidazol-2-yl)amino)-N-hydroxybenzamide (ID #7)

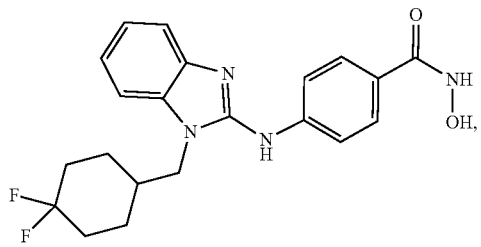

4-((1-((4,4-difluorocyclohexyl)methyl)-5-fluoro-1H-benzo[d]imidazol-2-yl)amino)-N-hydroxybenzamide (ID #8)

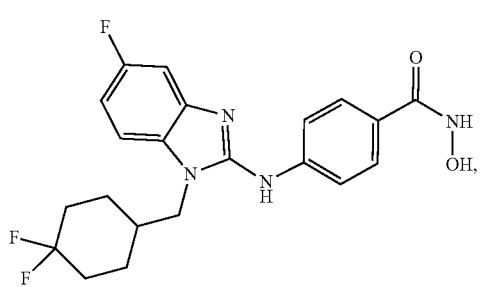 [SMILES: O=C(NO)c1ccc(Nc2nc3cc(F)ccc3n2CC2CCC(F)(F)CC2)cc1]

N-hydroxy-4-((1-((tetrahydro-2H-pyran-4-yl)methyl)-1H-benzo[d]imidazol-2-yl)amino)benzamide (ID #9)

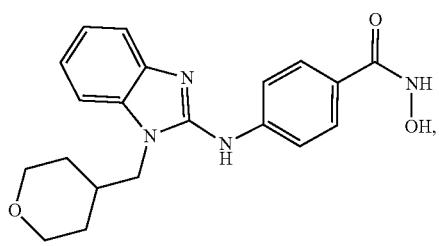 [SMILES: O=C(NO)c1ccc(Nc2nc3ccccc3n2CC2CCOCC2)cc1]

and
4-((5-fluoro-1-((tetrahydro-2H-pyran-4-yl)methyl)-1H-benzo[d]imidazol-2-yl)amino)-N-hydroxybenzamide (ID #10)

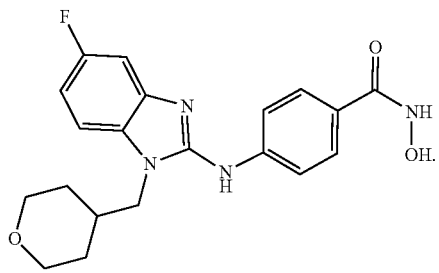 [SMILES: O=C(NO)c1ccc(Nc2nc3cc(F)ccc3n2CC2CCOCC2)cc1]

12. The method of claim 8, further comprising determining an expression signature in the subject that indicates the likely response to treatment with the compound, wherein the expression signature comprises expression of the HDAC isoform.

13. The method of claim 12, wherein the HDAC isoform is selected from the group consisting of: HDAC1, HDAC3, HDAC6, and HDAC10.

14. The method of claim 8, wherein the compound is administered at about 10-400 mg/kg.

15. The method of claim 4, wherein the compound is 4-((1-(cyclohexylmethyl)-1H-benzo[d]imidazol-2-yl)amino)-N-hydroxybenzamide (ID#1)

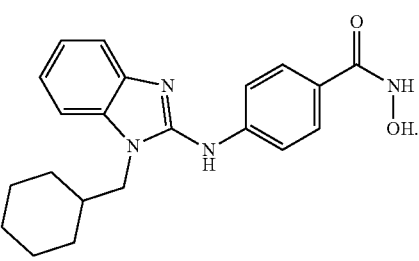 [SMILES: O=C(NO)c1ccc(Nc2nc3ccccc3n2CC2CCCCC2)cc1]

16. The method of claim 11, wherein the compound is 4-((1-(cyclohexylmethyl)-1H-benzo[d]imidazol-2-yl)amino)-N-hydroxybenzamide (ID#1)

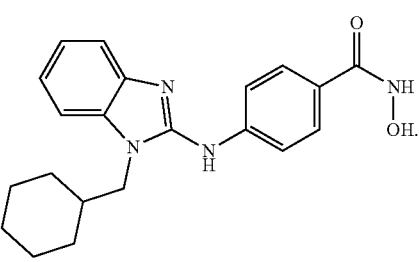 [SMILES: O=C(NO)c1ccc(Nc2nc3ccccc3n2CC2CCCCC2)cc1]

17. The method of claim 16, wherein the disease is breast cancer.

18. The method of claim 16, wherein the disease is non-small cell lung cancer (NSCLC).

19. The method of claim 16, wherein the disease is lymphoma.

20. The method of claim 16, wherein the disease is uterine cancer.

* * * * *